US009127286B2

(12) United States Patent
Nakazawa et al.

(10) Patent No.: US 9,127,286 B2
(45) Date of Patent: Sep. 8, 2015

(54) LONG-CHAIN TRANS-PRENYL DIPHOSPHATE SYNTHASE GENE

(75) Inventors: Yoshihisa Nakazawa, Osaka (JP); Yoko Harada, Osaka (JP); Hirotaka Uefuji, Osaka (JP); Ren Chen, Osaka (JP); Takeshi Bamba, Suita (JP); Akio Kobayashi, Suita (JP); Eiichiro Fukusaki, Suita (JP); Kazumasa Hirata, Suita (JP); Koichiro Gyokusen, Fukuoka (JP)

(73) Assignee: Hitachi Zosen Corporation, Osaka (JP)

( * ) Notice: Subject to any disclaimer, the term of this patent is extended or adjusted under 35 U.S.C. 154(b) by 990 days.

(21) Appl. No.: 12/550,863

(22) Filed: Aug. 31, 2009

(65) Prior Publication Data

US 2010/0218272 A1 Aug. 26, 2010

(30) Foreign Application Priority Data

Feb. 25, 2009 (JP) .................................. 2009-41759

(51) Int. Cl.
*C12N 15/82* (2006.01)
*C12N 9/10* (2006.01)
(52) U.S. Cl.
CPC .......... *C12N 15/8243* (2013.01); *C12N 9/1085* (2013.01)
(58) Field of Classification Search
USPC .............. 800/288, 298, 317.3; 536/23.2, 23.6
See application file for complete search history.

(56) References Cited

U.S. PATENT DOCUMENTS

| 6,174,715 | B1 | 1/2001 | Muramatsu et al. |
| 7,402,413 | B2 | 7/2008 | Matsuda et al. |
| 2004/0067566 | A1 | 4/2004 | Matsuda et al. |
| 2008/0064074 | A1 | 3/2008 | Matsuda et al. |
| 2009/0300794 | A1 | 12/2009 | Plesch et al. |

FOREIGN PATENT DOCUMENTS

| JP | 2004024275 A | 1/2004 |
| WO | 0240682 A1 | 5/2002 |
| WO | 02092811 A1 | 11/2002 |
| WO | 2007137973 A2 | 12/2007 |

OTHER PUBLICATIONS

Bamba, T. et al. Aug. 24, 2001; Osaka University Graduate School of Engineering, Department of Biotechnology database; GenBank Accesion gi: 15289749.*
Hirooka, K. et al. Biochem J. (2003) vol. 370, pp. 679-686.*
Takahashi, S. et al. FEBS Letters, vol. 580, (2006) pp. 955-959.*
Ohya, DR. Norimasa et al, "Biosynthesis of Natural Rubber and Other Natural Polyisoprenoids", Biopolymers, 2001, pp. 73-109, vol. 2, Wiley-VCH, Germany.
Bamba, Takeshi et al., "In-situ chemical analyses of trans-polyisoprene by histochemical staining and Fourier transform infrared microspectroscopy in a rubber-producing plant, *Eucommia ulmoides* Oliver", Planta, 2002, pp. 934-939, vol. 215, Springer-Verlag.
"Regarding Rubber", (on-line), Nihonkai Rubber Co., Ltd., <http://www.nihonkai-r.co.jp/semi02.htm>, 7 pp. and partial English translation (1 page).
Wang, Kevin et al., "Chain-length determination mechanism of isoprenyl diphosphate synthases and implications for molecular evolution", TIBS, Nov. 1999, pp. 445-451, vol. 24.
Koyama, Tanetoshi et al., "Unlocking the mystery of natural rubber biosynthesis—Mechanism of construction of isoprene chains inside a living body", Chemistry Today, 1990, pp. 42-49, vol. 237, with partial English translation (2 pp.).
Takahashi, Seiji et al., "Molecular analysis of the enzymes participating in isoprenoid biosynthesis", Kagaku to Seibutsu (Chemistry and Biology), 2005, pp. 296-304, vol. 43, with partial English translation.
Asawatreratanakul, Kasem et al., "Molecular cloning, expression and characterization of cDNA encoding cis-prenyltransferases from *Hevea brasiliensis*", Eur. J. Biochem, 2003, pp. 4671-4680, vol. 270.
Manzano, David et al., "The metabolic imbalance underlying lesion formation in *Arabidopsis thaliana* overexpressing farnesyl diphosphate synthase (isoform 1S) leads to oxidative stress and is triggered by the developmental decline of endogenous HMGR activity", Planta, 2004, pp. 982-992, vol. 219.
Takahashi, Sakiko et al., "Metabolic engineering of co-enzyme Q by modification of isoprenoid side chain in plant", FEBS Letters, 2006, pp. 955-959, vol. 580.
Bamba, Takeshi et al., "Mevalonate pathway is responsible for polyisoprenoid biosynthesis in *Eucommia ulmoides* Oliver", The Japanese Society for Chemical Regulation of Plants, 2002, pp. 29-30, vol. 37, English abstract attached.
Nakazawa, Yoshihisa et al., "Development of Production-Regulation Technology for Industrial Materials of Trans-type Rubber by Plants", Research Association for Biotechnology (heisei 17(2005)), The 23rd International Workshop, Plant Biotechnology for Production of Industrial Materials, 0091, pp. 7-10, with partial English translation.

* cited by examiner

*Primary Examiner* — Russell Kallis
(74) *Attorney, Agent, or Firm* — The Webb Law Firm

(57) ABSTRACT

A method for increasing the amount of trans-1,4-polyisoprene contained in a plant, and a method for effectively producing trans-1,4-polyisoprene using a plant are provided. A long-chain trans-prenyl diphosphate synthase gene that comprises DNA having at least one base sequence selected from the group consisting of a base sequence from positions 88 to 1134 of the base sequence of SEQ ID NO: 1 or a complementary sequence thereof, a base sequence from positions 42 to 1088 of the base sequence of SEQ ID NO: 3 or a complementary sequence thereof, and a base sequence from positions 91 to 1140 of the base sequence of SEQ ID NO: 5 or a complementary sequence thereof are disclosed; as well as a plant transformed with an expression vector containing the gene.

8 Claims, 8 Drawing Sheets

① cspA promoter
② lac operator
③ cspA 5'-UTR
④ TEE
⑤ His-Tag
⑥ TPL-encoding sequence
⑦ cspA 3'-UTR A: Before induction
B: After induction
C: Eluted fraction 35S: CaMV35S promoter
NOS: NOS promoter
nos: NOS terminator
I: Intron TPL1: TPL1-encoding sequence
NPT II: Kanamycin resistance gene
sGFP: Modified GFP gene 35S: CaMV35S promoter
35s: CaMV35S terminator
nos: NOS terminator TPL1: TPL1-encoding sequence
NPT II: Kanamycin resistance gene
GUS: β-glucuronidase gene

SEQUENCE LISTING

```
<160> NUMBER OF SEQ ID NOS: 31

<210> SEQ ID NO 1
<211> LENGTH: 1296
<212> TYPE: DNA
<213> ORGANISM: Eucommia ulmoides
<220> FEATURE:
<221> NAME/KEY: CDS
<222> LOCATION: (88)..(1134)
<223> OTHER INFORMATION:

<400> SEQUENCE: 1
acgctgtcct tgcacttggt agacctaaac cacaaccaaa ataaactctc tctctcagaa      60
```

| | |
|---|---|
| tactgcctct gtcgaaagct attaacc atg gcg aaa ctg aag aaa gaa ttt ctt<br>                                       Met Ala Glu Leu Lys Lys Glu Phe Leu<br>                                          1               5 | 114 |
| aac gtc tac tcg gtg ctg aaa aag gag ttg ctc cat gac cca gcc ttc<br>Asn Val Tyr Ser Val Leu Lys Lys Glu Leu Leu His Asp Pro Ala Phe<br>10                  15                    20                    25 | 162 |
| agc ctc act gaa gat tct cgc aat tgg gtc gaa cgg atg ttg gac tac<br>Ser Leu Thr Glu Asp Ser Arg Asn Trp Val Glu Arg Met Leu Asp Tyr<br>                  30                    35                    40 | 210 |
| aat gta ccc gga gga aaa ctg aat aga gga ctt tcc gtg gtg gac agc<br>Asn Val Pro Gly Gly Lys Leu Asn Arg Gly Leu Ser Val Val Asp Ser<br>                      45                    50                    55 | 258 |
| tac aag ctt ctg aag gaa ctg tca agt tca aag aaa gga gct caa ctc<br>Tyr Lys Leu Leu Lys Glu Leu Ser Ser Ser Lys Lys Gly Ala Gln Leu<br>        60                    65                    70 | 306 |
| act gag agc gaa ata ttt cat tca tct gtg ttg ggt tgg tgc att gag<br>Thr Glu Ser Glu Ile Phe His Ser Ser Val Leu Gly Trp Cys Ile Glu<br>75                    80                    85 | 354 |
| tgg ctt caa gct tgt gcg ctt gtt ctc gac gat att atg gac agc tca<br>Trp Leu Gln Ala Cys Ala Leu Val Leu Asp Asp Ile Met Asp Ser Ser<br>90                    95                   100               105 | 402 |
| cac aca cgc cga ggt caa atg tgt tgg tac aaa ctc ccc aag gtt ggt<br>His Thr Arg Arg Gly Gln Met Cys Trp Tyr Lys Leu Pro Lys Val Gly<br>                   110                   115               120 | 450 |
| atg att gct att aac gat ggg ctt ata ctt cgc aat cat gtg ccg agg<br>Met Ile Ala Ile Asn Asp Gly Leu Ile Leu Arg Asn His Val Pro Arg<br>              125                   130               135 | 498 |
| att ctc aag aaa cat ttt cga tcc aag cct tac tat ctc gaa ttg ttg<br>Ile Leu Lys Lys His Phe Arg Ser Lys Pro Tyr Tyr Leu Glu Leu Leu<br>           140                   145               150 | 546 |
| gat tta ttt cac gag gtg gaa tgt cag act gtt ggt gga caa atg att<br>Asp Leu Phe His Glu Val Glu Cys Gln Thr Val Gly Gly Gln Met Ile<br>155                    160                   165 | 594 |
| gat ttg att act aca ctt gta gga gag att gat cta tct gag tac tca<br>Asp Leu Ile Thr Thr Leu Val Gly Glu Ile Asp Leu Ser Glu Tyr Ser<br>170                   175                   180               185 | 642 |
| tta cct acc cat cgt caa att act gtc tca aaa acc tct tat tac tcg<br>Leu Pro Thr His Arg Gln Ile Thr Val Ser Lys Thr Ser Tyr Tyr Ser<br>           190                   195               200 | 690 |
| ttc tac ctt ccg gtg gct tgt gca ctt cta atg acc ggc gag aaa ttg<br>Phe Tyr Leu Pro Val Ala Cys Ala Leu Leu Met Thr Gly Glu Lys Leu<br>           205                   210               215 | 738 |
| gaa agc cac agt ggc atg aag gac ata ctt atc gaa atg gga agc tat<br>Glu Ser His Ser Gly Met Lys Asp Ile Leu Ile Glu Met Gly Ser Tyr<br>        220                   225               230 | 786 |
| ttt caa gtc cag gat gat tac ctg gat tgt ttt ggt gat cct gag gtg<br>Phe Gln Val Gln Asp Asp Tyr Leu Asp Cys Phe Gly Asp Pro Glu Val<br>        235                   240               245 | 834 |
| att gga aag att gga tca gat att gaa gat ttt aag tgc act tgg tta<br>Ile Gly Lys Ile Gly Ser Asp Ile Glu Asp Phe Lys Cys Thr Trp Leu<br>250                    255                   260               265 | 882 |
| gtc gta aaa gca ttg gaa ctt tgt aac gaa gaa caa aag aag att tta<br>Val Val Lys Ala Leu Glu Leu Cys Asn Glu Glu Gln Lys Lys Ile Leu<br>           270                   275               280 | 930 |
| tat gat aac tat gga aaa aaa gac cca gaa tct gtt gct aga gtg aag<br>Tyr Asp Asn Tyr Gly Lys Lys Asp Pro Glu Ser Val Ala Arg Val Lys<br>              285                   290               295 | 978 |
| gat ctt tat aaa act ctc aag ctt cag gac gtg ttc gag gag tac gag<br>Asp Leu Tyr Lys Thr Leu Lys Leu Gln Asp Val Phe Glu Glu Tyr Glu<br>           300                   305               310 | 1026 |

```
aaa aag acg cac gag aag cta aac aag tcg att gat gct tat cca agt    1074
Lys Lys Thr His Glu Lys Leu Asn Lys Ser Ile Asp Ala Tyr Pro Ser
315                 320                 325 aaa gca gtg caa gca gtt cta caa tca ttc ttg gct aag att cac agg    1122
Lys Ala Val Gln Ala Val Leu Gln Ser Phe Leu Ala Lys Ile His Arg
330                 335                 340                 345 agg ctc aag tag gaaggaagtg atttaatatg cctgcctgag ttaatccggt        1174
Arg Leu Lys aaatattaa atgaaataaa atgtattctt atttgctcag tagagcaaga ttgttgtctg   1234
ctatgttgtg aacattattt caggctttat tgcatatttg gttctccaaa aaaaaaaaa   1294 aa                                                                 1296

<210> SEQ ID NO 2
<211> LENGTH: 348
<212> TYPE: PRT
<213> ORGANISM: Eucommia ulmoides

<400> SEQUENCE: 2

Met Ala Glu Leu Lys Lys Glu Phe Leu Asn Val Tyr Ser Val Leu Lys
1               5                   10                  15

Lys Glu Leu Leu His Asp Pro Ala Phe Ser Leu Thr Glu Asp Ser Arg
            20                  25                  30

Asn Trp Val Glu Arg Met Leu Asp Tyr Asn Val Pro Gly Gly Lys Leu
        35                  40                  45

Asn Arg Gly Leu Ser Val Val Asp Ser Tyr Lys Leu Leu Lys Glu Leu
    50                  55                  60

Ser Ser Ser Lys Lys Gly Ala Gln Leu Thr Glu Ser Glu Ile Phe His
65                  70                  75                  80

Ser Ser Val Leu Gly Trp Cys Ile Glu Trp Leu Gln Ala Cys Ala Leu
                85                  90                  95

Val Leu Asp Asp Ile Met Asp Ser Ser His Thr Arg Arg Gly Gln Met
            100                 105                 110

Cys Trp Tyr Lys Leu Pro Lys Val Gly Met Ile Ala Ile Asn Asp Gly
        115                 120                 125

Leu Ile Leu Arg Asn His Val Pro Arg Ile Leu Lys Lys His Phe Arg
    130                 135                 140

Ser Lys Pro Tyr Tyr Leu Glu Leu Leu Asp Leu Phe His Glu Val Glu
145                 150                 155                 160

Cys Gln Thr Val Gly Gly Gln Met Ile Asp Leu Ile Thr Thr Leu Val
                165                 170                 175

Gly Glu Ile Asp Leu Ser Glu Tyr Ser Leu Pro Thr His Arg Gln Ile
            180                 185                 190

Thr Val Ser Lys Thr Ser Tyr Tyr Ser Phe Tyr Leu Pro Val Ala Cys
        195                 200                 205

Ala Leu Leu Met Thr Gly Glu Lys Leu Glu Ser His Ser Gly Met Lys
    210                 215                 220

Asp Ile Leu Ile Glu Met Gly Ser Tyr Phe Gln Val Gln Asp Asp Tyr
225                 230                 235                 240

Leu Asp Cys Phe Gly Asp Pro Glu Val Ile Gly Lys Ile Gly Ser Asp
                245                 250                 255

Ile Glu Asp Phe Lys Cys Thr Trp Leu Val Val Lys Ala Leu Glu Leu
            260                 265                 270

Cys Asn Glu Glu Gln Lys Lys Ile Leu Tyr Asp Asn Tyr Gly Lys Lys
        275                 280                 285
```

```
Asp Pro Glu Ser Val Ala Arg Val Lys Asp Leu Tyr Lys Thr Leu Lys
    290                 295                 300

Leu Gln Asp Val Phe Glu Tyr Glu Lys Lys Thr His Glu Lys Leu
305                 310                 315                 320

Asn Lys Ser Ile Asp Ala Tyr Pro Ser Lys Ala Val Gln Ala Val Leu
                325                 330                 335

Gln Ser Phe Leu Ala Lys Ile His Arg Arg Leu Lys
            340                 345

<210> SEQ ID NO 3
<211> LENGTH: 1332
<212> TYPE: DNA
<213> ORGANISM: Eucommia ulmoides
<220> FEATURE:
<221> NAME/KEY: CDS
<222> LOCATION: (42)..(1088)
<223> OTHER INFORMATION:

<400> SEQUENCE: 3
cggcctttcg ttctctctct ctctctttga gtaatatatc c atg acc gag ctg aag          56
                                            Met Thr Glu Leu Lys
                                              1               5 agc aaa ttt gtc aag gtt tac tct gtg cta aaa aag gaa ctc ctc cat          104
Ser Lys Phe Val Lys Val Tyr Ser Val Leu Lys Lys Glu Leu Leu His
            10                  15                  20 gat tca gca ttc gga ctc acg gat gat tct cgc aat tgg gtt gag cgg          152
Asp Ser Ala Phe Gly Leu Thr Asp Asp Ser Arg Asn Trp Val Glu Arg
        25                  30                  35 ata atg gac tac aat gta cca gga gga aag cta aat cga ggg ctc tct          200
Ile Met Asp Tyr Asn Val Pro Gly Gly Lys Leu Asn Arg Gly Leu Ser
    40                  45                  50 gtt gtt gat agc tat aag tta cta cga gaa cta act aat tct aaa tac          248
Val Val Asp Ser Tyr Lys Leu Leu Arg Glu Leu Thr Asn Ser Lys Tyr
55                  60                  65 aaa agt gaa ttg agt gat gat gaa att ttt ctt gca tcc gtg ctt ggt          296
Lys Ser Glu Leu Ser Asp Asp Glu Ile Phe Leu Ala Ser Val Leu Gly
70                  75                  80                  85 tgg agt gtt gag tgg atc caa gca tgt gct ctt gtt ctt gat gat att          344
Trp Ser Val Glu Trp Ile Gln Ala Cys Ala Leu Val Leu Asp Asp Ile
                90                  95                  100 atg gat cat tcg cac aca cgt cgt ggt cac cct tgt tgg ttt aga ttg          392
Met Asp His Ser His Thr Arg Arg Gly His Pro Cys Trp Phe Arg Leu
            105                 110                 115 ccc aag gtt ggc atg att gct ata aat gat ggc ttg ata ctt cgc aac          440
Pro Lys Val Gly Met Ile Ala Ile Asn Asp Gly Leu Ile Leu Arg Asn
        120                 125                 130 cat gta cca cga att ctt agg act cat ttc caa aca gaa cat tat tac          488
His Val Pro Arg Ile Leu Arg Thr His Phe Gln Thr Glu His Tyr Tyr
    135                 140                 145 ctt caa ctg gtt gat tta ttt cac gag gta gag tgt cag aca att gca          536
Leu Gln Leu Val Asp Leu Phe His Glu Val Glu Cys Gln Thr Ile Ala
150                 155                 160                 165 gga caa atg ttg gat ttg atc acc acg ctc gca gga gag att aac cta          584
Gly Gln Met Leu Asp Leu Ile Thr Thr Leu Ala Gly Glu Ile Asn Leu
                170                 175                 180 tca agt tac tcg ttg cct gtg tac caa caa att act ctg tcc aaa aca          632
Ser Ser Tyr Ser Leu Pro Val Tyr Gln Gln Ile Thr Leu Ser Lys Thr
            185                 190                 195 tct tat tat tca ttt tat ctt ccg gtt gca tgt gca ctc gtt atg ttg          680
Ser Tyr Tyr Ser Phe Tyr Leu Pro Val Ala Cys Ala Leu Val Met Leu
```

```
              200                 205                 210
ggt gaa aac ttg gaa agt cac gat gac atg aag gac ata ctt ctt gaa      728
Gly Glu Asn Leu Glu Ser His Asp Asp Met Lys Asp Ile Leu Leu Glu
    215                 220                 225 atg gga acc tat ttc caa gta cag gat gat tat ctt gat tgt ttt ggg      776
Met Gly Thr Tyr Phe Gln Val Gln Asp Asp Tyr Leu Asp Cys Phe Gly
230                 235                 240                 245 gat cca gag gtg att ggt aag att ggc acg gat ata gaa gat aat aag      824
Asp Pro Glu Val Ile Gly Lys Ile Gly Thr Asp Ile Glu Asp Asn Lys
                250                 255                 260 tgc act tgg ttg gta gta caa gca ctg gag cac tgt aat gaa gaa caa      872
Cys Thr Trp Leu Val Val Gln Ala Leu Glu His Cys Asn Glu Glu Gln
            265                 270                 275 aag aag tta cta tat gat aac tat gga aga aag gat cca aaa caa gtt      920
Lys Lys Leu Leu Tyr Asp Asn Tyr Gly Arg Lys Asp Pro Lys Gln Val
        280                 285                 290 gca aaa gtg aag gag ctc tat aaa act cta aat ctt gag gat tta ttt      968
Ala Lys Val Lys Glu Leu Tyr Lys Thr Leu Asn Leu Glu Asp Leu Phe
    295                 300                 305 acc cag tat gag aac aag act tgc aag aag ctc aca aag tcc att gaa     1016
Thr Gln Tyr Glu Asn Lys Thr Cys Lys Lys Leu Thr Lys Ser Ile Glu
310                 315                 320                 325 gct ctc cca aat gta gca gta caa gca gtt cta aaa tcg ttc ttg gct     1064
Ala Leu Pro Asn Val Ala Val Gln Ala Val Leu Lys Ser Phe Leu Ala
                330                 335                 340 aag ata cac aag agg ctc aag tag ggacctcaca aaaagtgttc ccaatgatcc    1118
Lys Ile His Lys Arg Leu Lys
                345 tttgtttaag tagtggcggt gttagttttg cttttttatg ctcttcgtat ttcttgtttg   1178 agtgctttcc ttgttttggt tgctgcttat aattttttctt tttcaatttc tggaagactt   1238 cgaacctgaa taaatgtagt cgttaagaat gtaaattata ttttcttaaa cttgtcaaat    1298 tctttggttt tgattgaaaa aaaaaaaaaa aaaa                                1332

<210> SEQ ID NO 4
<211> LENGTH: 348
<212> TYPE: PRT
<213> ORGANISM: Eucommia ulmoides

<400> SEQUENCE: 4

Met Thr Glu Leu Lys Ser Lys Phe Val Lys Val Tyr Ser Val Leu Lys
1               5                   10                  15

Lys Glu Leu Leu His Asp Ser Ala Phe Gly Leu Thr Asp Asp Ser Arg
            20                  25                  30

Asn Trp Val Glu Arg Ile Met Asp Tyr Asn Val Pro Gly Gly Lys Leu
        35                  40                  45

Asn Arg Gly Leu Ser Val Val Asp Ser Tyr Lys Leu Leu Arg Glu Leu
    50                  55                  60

Thr Asn Ser Lys Tyr Lys Ser Glu Leu Ser Asp Asp Glu Ile Phe Leu
65                  70                  75                  80

Ala Ser Val Leu Gly Trp Ser Val Glu Trp Ile Gln Ala Cys Ala Leu
                85                  90                  95

Val Leu Asp Asp Ile Met Asp His Ser His Thr Arg Arg Gly His Pro
            100                 105                 110

Cys Trp Phe Arg Leu Pro Lys Val Gly Met Ile Ala Ile Asn Asp Gly
        115                 120                 125

Leu Ile Leu Arg Asn His Val Pro Arg Ile Leu Arg Thr His Phe Gln
```

```
            130                 135                 140
Thr Glu His Tyr Tyr Leu Gln Leu Val Asp Leu Phe His Glu Val Glu
145                 150                 155                 160

Cys Gln Thr Ile Ala Gly Gln Met Leu Asp Leu Ile Thr Thr Leu Ala
                165                 170                 175

Gly Glu Ile Asn Leu Ser Ser Tyr Ser Leu Pro Val Tyr Gln Gln Ile
                180                 185                 190

Thr Leu Ser Lys Thr Ser Tyr Tyr Ser Phe Tyr Leu Pro Val Ala Cys
            195                 200                 205

Ala Leu Val Met Leu Gly Glu Asn Leu Glu Ser His Asp Asp Met Lys
        210                 215                 220

Asp Ile Leu Leu Glu Met Gly Thr Tyr Phe Gln Val Gln Asp Asp Tyr
225                 230                 235                 240

Leu Asp Cys Phe Gly Asp Pro Glu Val Ile Gly Lys Ile Gly Thr Asp
                245                 250                 255

Ile Glu Asp Asn Lys Cys Thr Trp Leu Val Val Gln Ala Leu Glu His
                260                 265                 270

Cys Asn Glu Glu Gln Lys Lys Leu Leu Tyr Asp Asn Tyr Gly Arg Lys
            275                 280                 285

Asp Pro Lys Gln Val Ala Lys Val Lys Glu Leu Tyr Lys Thr Leu Asn
        290                 295                 300

Leu Glu Asp Leu Phe Thr Gln Tyr Glu Asn Lys Thr Cys Lys Lys Leu
305                 310                 315                 320

Thr Lys Ser Ile Glu Ala Leu Pro Asn Val Ala Val Gln Ala Val Leu
                325                 330                 335

Lys Ser Phe Leu Ala Lys Ile His Lys Arg Leu Lys
            340                 345

<210> SEQ ID NO 5
<211> LENGTH: 1353
<212> TYPE: DNA
<213> ORGANISM: Eucommia ulmoides
<220> FEATURE:
<221> NAME/KEY: CDS
<222> LOCATION: (91)..(1140)
<223> OTHER INFORMATION:

<400> SEQUENCE: 5
gatcaacaca tccttgagcg ttaccgcctt cccttcgtt ctctatcata ttcttaggtc      60
catcaattgc tgccttttcg ctcagaatta atg gcg gaa acg acc caa cca aaa    114
                                   Met Ala Glu Thr Thr Gln Pro Lys
                                     1               5 ttt cac agc gtt tac tca gtt ctg aaa gcg gag ctt ctc cag gac ccc    162
Phe His Ser Val Tyr Ser Val Leu Lys Ala Glu Leu Leu Gln Asp Pro
        10                  15                  20 gtc ttc gac ctc act gac gaa tca cgt aaa tgg gtt gat cgg atg atg    210
Val Phe Asp Leu Thr Asp Glu Ser Arg Lys Trp Val Asp Arg Met Met
25                  30                  35                  40 gat tat aat gta cct gga gga aag tgc aac cga ggg cta tct gtt agt    258
Asp Tyr Asn Val Pro Gly Gly Lys Cys Asn Arg Gly Leu Ser Val Ser
                45                  50                  55 gac agc tat aag ttg atg aaa gag cta act gat cat aaa aaa ggg aaa    306
Asp Ser Tyr Lys Leu Met Lys Glu Leu Thr Asp His Lys Lys Gly Lys
            60                  65                  70 gaa cta agt gat gat gaa gtt ttt ctc tcc tcc gtc ctt ggt tgg tgt    354
Glu Leu Ser Asp Asp Glu Val Phe Leu Ser Ser Val Leu Gly Trp Cys
        75                  80                  85
```

```
atc gaa tgg atg caa gcg tgt gca ctt ctt ctt gat gat atc atg gat    402
Ile Glu Trp Met Gln Ala Cys Ala Leu Leu Leu Asp Asp Ile Met Asp
 90              95                 100 agt tca cac acg cgt cga gga cat ata tgt tgg tac aaa caa ccc aag    450
Ser Ser His Thr Arg Arg Gly His Ile Cys Trp Tyr Lys Gln Pro Lys
105             110                 115                 120 gtt ggg atg att gcg ata aat gat ggt cta atg ctt cga aac cat gtc    498
Val Gly Met Ile Ala Ile Asn Asp Gly Leu Met Leu Arg Asn His Val
            125                 130                 135 ccg aga ata ttg agg aag cat ttt cgg acc aaa cct tat tat ctt gaa    546
Pro Arg Ile Leu Arg Lys His Phe Arg Thr Lys Pro Tyr Tyr Leu Glu
            140                 145                 150 ttg cta gat tta ttt cat gag gtc gaa tgc caa aca gtg gct ggg cag    594
Leu Leu Asp Leu Phe His Glu Val Glu Cys Gln Thr Val Ala Gly Gln
            155                 160                 165 atg ata gat cta att acc aca ctt ctc gga gag gcc gat tta tca gaa    642
Met Ile Asp Leu Ile Thr Thr Leu Leu Gly Glu Ala Asp Leu Ser Glu
170                 175                 180 tac aaa tac cca att cat gaa cga att gtg gtt gca aaa aca gct tat    690
Tyr Lys Tyr Pro Ile His Glu Arg Ile Val Val Ala Lys Thr Ala Tyr
185                 190                 195                 200 tac tct ttt tac ctt ccg gtg gct tgc gca ctt ctg atg tcg ggc gag    738
Tyr Ser Phe Tyr Leu Pro Val Ala Cys Ala Leu Leu Met Ser Gly Glu
                205                 210                 215 aaa cta gaa act cat agt ggc atg aag gac ata cta atc gaa atg ggg    786
Lys Leu Glu Thr His Ser Gly Met Lys Asp Ile Leu Ile Glu Met Gly
                220                 225                 230 acc tat ttt caa gct caa gat gat gtc att gat tgt ttt ggt gat cca    834
Thr Tyr Phe Gln Ala Gln Asp Asp Val Ile Asp Cys Phe Gly Asp Pro
        235                 240                 245 gag gtg atc ggc aag att gga aca gat att gaa gat tgt aag tgc act    882
Glu Val Ile Gly Lys Ile Gly Thr Asp Ile Glu Asp Cys Lys Cys Thr
        250                 255                 260 tgg tta gtc gtg aaa gca cta gaa ctt tgt gat gaa gaa caa aaa aag    930
Trp Leu Val Val Lys Ala Leu Glu Leu Cys Asp Glu Glu Gln Lys Lys
265                 270                 275                 280 ata cta tat gat aat tat gga aaa gac gat cca gat tgt gta gca aaa    978
Ile Leu Tyr Asp Asn Tyr Gly Lys Asp Asp Pro Asp Cys Val Ala Lys
                285                 290                 295 gtg aag gag ctt tat aag aca ctc aaa att cag gaa atc ttt gaa gag   1026
Val Lys Glu Leu Tyr Lys Thr Leu Lys Ile Gln Glu Ile Phe Glu Glu
                300                 305                 310 tat gag aca aag gaa tat gaa aaa tta act aag tca att gat gct tat   1074
Tyr Glu Thr Lys Glu Tyr Glu Lys Leu Thr Lys Ser Ile Asp Ala Tyr
            315                 320                 325 cca agc aaa gct gta ggg gca gtg tta aag tca ttc ttg gca aag atc   1122
Pro Ser Lys Ala Val Gly Ala Val Leu Lys Ser Phe Leu Ala Lys Ile
330                 335                 340 tat cgg agg cat tat tga aaatacagtt atttaaggtg aatatttgt           1170
Tyr Arg Arg His Tyr
345 ggattgaagc gtcaaatgtg agaaaggctt aaagattgtg tgtattttca ggaattccaa    1230 tgtgtgtgat ttggtgtgcc ataatttata attaatgatt tgagtgatga aaatattgta    1290 tttgagggaa caaataaatt gcaacgacta actatttttt aattaaccaa aaaaaaaaaa    1350 aaa                                                                  1353

<210> SEQ ID NO 6
<211> LENGTH: 349
```

<212> TYPE: PRT
<213> ORGANISM: Eucommia ulmoides

<400> SEQUENCE: 6

Met Ala Glu Thr Thr Gln Pro Lys Phe His Ser Val Tyr Ser Val Leu
1               5                   10                  15

Lys Ala Glu Leu Leu Gln Asp Pro Val Phe Asp Leu Thr Asp Glu Ser
            20                  25                  30

Arg Lys Trp Val Asp Arg Met Met Asp Tyr Asn Val Pro Gly Gly Lys
        35                  40                  45

Cys Asn Arg Gly Leu Ser Val Ser Asp Ser Tyr Lys Leu Met Lys Glu
    50                  55                  60

Leu Thr Asp His Lys Lys Gly Lys Glu Leu Ser Asp Asp Glu Val Phe
65                  70                  75                  80

Leu Ser Ser Val Leu Gly Trp Cys Ile Glu Trp Met Gln Ala Cys Ala
                85                  90                  95

Leu Leu Leu Asp Asp Ile Met Asp Ser Ser His Thr Arg Arg Gly His
            100                 105                 110

Ile Cys Trp Tyr Lys Gln Pro Lys Val Gly Met Ile Ala Ile Asn Asp
        115                 120                 125

Gly Leu Met Leu Arg Asn His Val Pro Arg Ile Leu Arg Lys His Phe
    130                 135                 140

Arg Thr Lys Pro Tyr Tyr Leu Glu Leu Leu Asp Leu Phe His Glu Val
145                 150                 155                 160

Glu Cys Gln Thr Val Ala Gly Gln Met Ile Asp Leu Ile Thr Thr Leu
                165                 170                 175

Leu Gly Glu Ala Asp Leu Ser Glu Tyr Lys Tyr Pro Ile His Glu Arg
            180                 185                 190

Ile Val Val Ala Lys Thr Ala Tyr Tyr Ser Phe Tyr Leu Pro Val Ala
        195                 200                 205

Cys Ala Leu Leu Met Ser Gly Glu Lys Leu Glu Thr His Ser Gly Met
    210                 215                 220

Lys Asp Ile Leu Ile Glu Met Gly Thr Tyr Phe Gln Ala Gln Asp Asp
225                 230                 235                 240

Val Ile Asp Cys Phe Gly Asp Pro Glu Val Ile Gly Lys Ile Gly Thr
                245                 250                 255

Asp Ile Glu Asp Cys Lys Cys Thr Trp Leu Val Val Lys Ala Leu Glu
            260                 265                 270

Leu Cys Asp Glu Glu Gln Lys Lys Ile Leu Tyr Asp Asn Tyr Gly Lys
        275                 280                 285

Asp Asp Pro Asp Cys Val Ala Lys Val Lys Glu Leu Tyr Lys Thr Leu
    290                 295                 300

Lys Ile Gln Glu Ile Phe Glu Glu Tyr Glu Thr Lys Glu Tyr Glu Lys
305                 310                 315                 320

Leu Thr Lys Ser Ile Asp Ala Tyr Pro Ser Lys Ala Val Gly Ala Val
                325                 330                 335

Leu Lys Ser Phe Leu Ala Lys Ile Tyr Arg Arg His Tyr
            340                 345

<210> SEQ ID NO 7
<211> LENGTH: 23
<212> TYPE: DNA
<213> ORGANISM: Artificial
<220> FEATURE:
<223> OTHER INFORMATION: TPL1 degenerate 1st sense primer
<220> FEATURE:

<221> NAME/KEY: misc_feature
<222> LOCATION: (2)..(2)
<223> OTHER INFORMATION: n=inosine
<220> FEATURE:
<221> NAME/KEY: misc_feature
<222> LOCATION: (5)..(5)
<223> OTHER INFORMATION: n=inosine
<220> FEATURE:
<221> NAME/KEY: misc_feature
<222> LOCATION: (8)..(8)
<223> OTHER INFORMATION: n=inosine
<220> FEATURE:
<221> NAME/KEY: misc_feature
<222> LOCATION: (17)..(17)
<223> OTHER INFORMATION: n=nucleotide

<400> SEQUENCE: 7
cnytnggntg gtgyrtngar tgg    23

<210> SEQ ID NO 8
<211> LENGTH: 26
<212> TYPE: DNA
<213> ORGANISM: Artificial
<220> FEATURE:
<223> OTHER INFORMATION: TPL1 degenerate 1st antisense primer
<220> FEATURE:
<221> NAME/KEY: misc_feature
<222> LOCATION: (6)..(6)
<223> OTHER INFORMATION: n=nucleotide
<220> FEATURE:
<221> NAME/KEY: misc_feature
<222> LOCATION: (15)..(15)
<223> OTHER INFORMATION: n=inosine
<220> FEATURE:
<221> NAME/KEY: misc_feature
<222> LOCATION: (18)..(18)
<223> OTHER INFORMATION: n=inosine
<220> FEATURE:
<221> NAME/KEY: misc_feature
<222> LOCATION: (19)..(19)
<223> OTHER INFORMATION: n=inosine
<220> FEATURE:
<221> NAME/KEY: misc_feature
<222> LOCATION: (21)..(21)
<223> OTHER INFORMATION: n=inosine
<220> FEATURE:
<221> NAME/KEY: misc_feature
<222> LOCATION: (24)..(24)
<223> OTHER INFORMATION: n=inosine

<400> SEQUENCE: 8
gtycangtyc trctnatnna nctnac    26

<210> SEQ ID NO 9
<211> LENGTH: 22
<212> TYPE: DNA
<213> ORGANISM: Artificial
<220> FEATURE:
<223> OTHER INFORMATION: TPL1 degenerate 2nd sense primer
<220> FEATURE:
<221> NAME/KEY: misc_feature
<222> LOCATION: (5)..(5)
<223> OTHER INFORMATION: n=inosine
<220> FEATURE:
<221> NAME/KEY: misc_feature
<222> LOCATION: (8)..(8)
<223> OTHER INFORMATION: n=inosine
<220> FEATURE:
<221> NAME/KEY: misc_feature
<222> LOCATION: (17)..(17)
<223> OTHER INFORMATION: n=nucleotide

<400> SEQUENCE: 9
ggtgnrtnga rtggytncar gc    22

<210> SEQ ID NO 10
<211> LENGTH: 23
<212> TYPE: DNA
<213> ORGANISM: Artificial
<220> FEATURE:
<223> OTHER INFORMATION: TPL1 degenerate 2nd antisense primer
<220> FEATURE:
<221> NAME/KEY: misc_feature
<222> LOCATION: (4)..(4)
<223> OTHER INFORMATION: n=nucleotide
<220> FEATURE:
<221> NAME/KEY: misc_feature
<222> LOCATION: (7)..(7)
<223> OTHER INFORMATION: n=nucleotide
<220> FEATURE:
<221> NAME/KEY: misc_feature
<222> LOCATION: (13)..(13)
<223> OTHER INFORMATION: n=inosine
<220> FEATURE:
<221> NAME/KEY: misc_feature
<222> LOCATION: (16)..(16)
<223> OTHER INFORMATION: n=inosine
<220> FEATURE:
<221> NAME/KEY: misc_feature
<222> LOCATION: (19)..(19)
<223> OTHER INFORMATION: n=inosine
<220> FEATURE:
<221> NAME/KEY: misc_feature
<222> LOCATION: (22)..(22)
<223> OTHER INFORMATION: n=inosine

<400> SEQUENCE: 10
cccntrnatr aangtncang tnc                                           23

<210> SEQ ID NO 11
<211> LENGTH: 21
<212> TYPE: DNA
<213> ORGANISM: Artificial
<220> FEATURE:
<223> OTHER INFORMATION: TPL1 probe sense primer

<400> SEQUENCE: 11
gtgctcttgt tcttgatgat a                                             21

<210> SEQ ID NO 12
<211> LENGTH: 21
<212> TYPE: DNA
<213> ORGANISM: Artificial
<220> FEATURE:
<223> OTHER INFORMATION: TPL1 probe antisense primer

<400> SEQUENCE: 12
caagaagtat gtccttcatg t                                             21

<210> SEQ ID NO 13
<211> LENGTH: 22
<212> TYPE: DNA
<213> ORGANISM: Artificial
<220> FEATURE:
<223> OTHER INFORMATION: TPL5 1st sense primer

<400> SEQUENCE: 13
acagtggctg ggcagatgat ag                                            22

<210> SEQ ID NO 14
<211> LENGTH: 22
<212> TYPE: DNA
<213> ORGANISM: Artificial
<220> FEATURE:

<223> OTHER INFORMATION: TPL5 2nd sense primer

<400> SEQUENCE: 14
ttaccacact tctcggagag gc                                    22

<210> SEQ ID NO 15
<211> LENGTH: 23
<212> TYPE: DNA
<213> ORGANISM: Artificial
<220> FEATURE:
<223> OTHER INFORMATION: TPL5 2nd antisense primer

<400> SEQUENCE: 15
cgcttgcatc cattcgatac acc                                   23

<210> SEQ ID NO 16
<211> LENGTH: 18
<212> TYPE: DNA
<213> ORGANISM: Artificial
<220> FEATURE:
<223> OTHER INFORMATION: TPL1 expression sense primer

<400> SEQUENCE: 16
acgctgtcct tgcacttg                                         18

<210> SEQ ID NO 17
<211> LENGTH: 27
<212> TYPE: DNA
<213> ORGANISM: Artificial
<220> FEATURE:
<223> OTHER INFORMATION: TPL1 expression antisense primer

<400> SEQUENCE: 17
ggagaaccaa atatgcaata aagcctg                               27

<210> SEQ ID NO 18
<211> LENGTH: 26
<212> TYPE: DNA
<213> ORGANISM: Artificial
<220> FEATURE:
<223> OTHER INFORMATION: TPL3 expression sense primer

<400> SEQUENCE: 18
ggcctttcgt tctctctctc tctctt                                26

<210> SEQ ID NO 19
<211> LENGTH: 28
<212> TYPE: DNA
<213> ORGANISM: Artificial
<220> FEATURE:
<223> OTHER INFORMATION: TPL3 expression anitsense primer

<400> SEQUENCE: 19
acgactacat ttattcaggt tcgaagtc                              28

<210> SEQ ID NO 20
<211> LENGTH: 25
<212> TYPE: DNA
<213> ORGANISM: Artificial
<220> FEATURE:
<223> OTHER INFORMATION: TPL5 expression sense primer

<400> SEQUENCE: 20
gatcaacaca tccttgagcg ttacc                                 25

```
<210> SEQ ID NO 21
<211> LENGTH: 29
<212> TYPE: DNA
<213> ORGANISM: Artificial
<220> FEATURE:
<223> OTHER INFORMATION: TPL5 expression anitsense primer

<400> SEQUENCE: 21
gttagtcgtt gcaatttatt tgttccctc                                29

<210> SEQ ID NO 22
<211> LENGTH: 35
<212> TYPE: DNA
<213> ORGANISM: Artificial
<220> FEATURE:
<223> OTHER INFORMATION: TPL1 expression sense NdeI primer

<400> SEQUENCE: 22
gagagagcat atggcggaac tgaagaaaga atttc                         35

<210> SEQ ID NO 23
<211> LENGTH: 35
<212> TYPE: DNA
<213> ORGANISM: Artificial
<220> FEATURE:
<223> OTHER INFORMATION: TPL1 expression antisense XhoI primer

<400> SEQUENCE: 23
ccgctcgagc tacttgagcc tcctgtgaat cttag                         35

<210> SEQ ID NO 24
<211> LENGTH: 35
<212> TYPE: DNA
<213> ORGANISM: Artificial
<220> FEATURE:
<223> OTHER INFORMATION: TPL3 expression sense NdeI primer

<400> SEQUENCE: 24
gagagagcat atgaccgagc tgaagagcaa atttg                         35

<210> SEQ ID NO 25
<211> LENGTH: 36
<212> TYPE: DNA
<213> ORGANISM: Artificial
<220> FEATURE:
<223> OTHER INFORMATION: TPL3 expression antisense XhoI primer

<400> SEQUENCE: 25
ccgctcgagc tacttgagcc tcttgtgtat cttagc                        36

<210> SEQ ID NO 26
<211> LENGTH: 28
<212> TYPE: DNA
<213> ORGANISM: Artificial
<220> FEATURE:
<223> OTHER INFORMATION: TPL5 expression sense NdeI primer

<400> SEQUENCE: 26
gagagagcat atggcggaaa cgacccaa                                 28

<210> SEQ ID NO 27
<211> LENGTH: 36
<212> TYPE: DNA
<213> ORGANISM: Artificial
<220> FEATURE:
<223> OTHER INFORMATION: TPL5 expression antisense XhoI primer
```

```
<400> SEQUENCE: 27
ccgctcgagt caataatgcc tccgatagat ctttgc                              36

<210> SEQ ID NO 28
<211> LENGTH: 23
<212> TYPE: DNA
<213> ORGANISM: Artificial
<220> FEATURE:
<223> OTHER INFORMATION: TPL1 quantification sense primer

<400> SEQUENCE: 28
aaggagctca actcactgag agc                                            23

<210> SEQ ID NO 29
<211> LENGTH: 20
<212> TYPE: DNA
<213> ORGANISM: Artificial
<220> FEATURE:
<223> OTHER INFORMATION: TPL1 quantification antisense primer

<400> SEQUENCE: 29
aatgcaccaa cccaacacag                                                20

<210> SEQ ID NO 30
<211> LENGTH: 19
<212> TYPE: DNA
<213> ORGANISM: Artificial
<220> FEATURE:
<223> OTHER INFORMATION: EF1a quantification sense primer

<400> SEQUENCE: 30
ccgagcgtga acgtggtat                                                 19

<210> SEQ ID NO 31
<211> LENGTH: 25
<212> TYPE: DNA
<213> ORGANISM: Artificial
<220> FEATURE:
<223> OTHER INFORMATION: EF1a quantification anitsense primer

<400> SEQUENCE: 31
tagtacttgg tggtttcgaa tttcc                                          25
```

LONG-CHAIN TRANS-PRENYL DIPHOSPHATE SYNTHASE GENE

BACKGROUND OF THE INVENTION

1. Field of the Invention

The present invention relates to a long-chain trans-prenyl diphosphate synthase gene, a plant transformed with an expression vector containing the gene, and a method for producing trans-1,4-polyisoprene using the plant.

2. Description of the Related Art

Polyisoprene (rubber), which is one of isoprenoid compounds, is classified into the cis-form and the trans-form according to the way in which isoprene units are polymerized. It is known that there are many plants that produce long-chain cis-polyisoprene (cis-1,4-polyisoprene), such as *Hevea brasiliensis* belonging to the family Euphorbiaceae, and *Taraxacum* and *Lactuca indica* belonging to the family Asteraceae. Among these, cis-1,4-polyisoprene produced by *Hevea brasiliensis* is commonly used commercially as a natural rubber (N. Ohya and T. Koyama, "Biosynthesis of natural rubber and other natural polyisoprenoids", *Biopolymers*, (Germany), WILEY-VCH, 2001, vol. 2, p. 73-109). On the other hand, it is known that there are a small number of plants that naturally produce long-chain trans-polyisoprene (trans-1,4-polyisoprene), such as *Eucommia ulmoides* belonging to the family Eucommiaceae, *Periploca sepium* belonging to the family Apocynaceae, and *Mimusops balata* and *Palaquium gutta* belonging to the family Sapotaceae, but they are not commercially used (T. Bamba et al., "In-situ chemical analyses of trans-polyisoprene by histochemical staining and Fourier transform infrared microspectroscopy in a rubber-producing plant, *Eucommia ulmoides Oliver*", *Planta*, 2002, vol. 215, p. 934-939). Among these, *Eucommia ulmoides*, which is a woody plant native to China, produces fibrous trans-1,4-polyisoprene. The leaves, bark, and peel of *Eucommia ulmoides* contain a large amount of trans-1,4-polyisoprene (T. Bamba et al.). However, currently, trans-1,4-polyisoprene is chemically synthesized, and used for outer layers of golf ball, plaster casts, sports protectors, and the like. Trans-1,4-polyisoprene is a thermoplastic elastomer having a low-melting point and high elasticity, and is also useful as an insulating material. Here, the word "natural rubber" commonly refers to a natural product-derived rubber in general, but may industrially refer to only a cis-rubber obtained from *Hevea brasiliensis*. It is not rare for higher plants to produce a rubber, and approximately 500 types of plants are confirmed to contain a rubber ("Regarding Rubber", (online), Nihonkai Rubber Co., Ltd., (accessed on Sep. 2, 2008), the Internet <http://www.nihonkair.co.jp/semi02.htm>).

All natural isoprenoid compounds are biosynthesized using, as an intermediate, prenyl diphosphate in which isoprene units having five carbon atoms (C5) are continuously linked, and all prenyl diphosphates are biosynthesized by prenyl diphosphate synthases (K. Wang and S. Ohnuma, "Chain-length determination mechanism of isoprenyl diphosphate synthases and implications for molecular evolution", TIBS, 1999, vol. 24, p. 445-4.51, and Tonetoshi Koyama and Kyozo Ogura, "Unlocking the mystery of natural rubber biosynthesis—Mechanism of construction of isoprene chains inside a living body", *Chemistry Today*, 1990, vol. 237, p. 42-49). Prenyl diphosphate synthase is a general term for enzymes that produce prenyl diphosphate having a larger number of isoprene units (a longer chain length) than that of a primer substrate, by catalyzing a reaction that condenses isopentenyl diphosphate (IPP), which is a compound having five carbon atoms (C5), to prenyl diphosphate (an allyl substrate) functioning as a primer substrate (Japanese Laid-Open Patent Publication No. 2004-24275). The prenyl diphosphate synthase is also referred to as a prenyl transferase or a prenyl chain-elongating enzyme (Seiji Takahashi and Tanetoshi Koyama, "Molecular analysis of the enzymes participating in isoprenoid biosynthesis", *Kagaku To Seibutsu* (*Chemistry and Biology*), 2005, vol. 43, p. 296-304).

IPP, which is a substrate for a prenyl diphosphate synthase, is biosynthesized by the mevalonate pathway or the like. Parts of the gene clusters for the enzymes participating in the mevalonate pathway have been clarified in various plants, such as *Eucommia ulmoides*.

Prenyl diphosphate synthases can be classified into enzymes that catalyze a condensation reaction that forms an E form (trans-form) double bond, and enzymes that catalyze a condensation reaction that forms a Z form (cis-form) double bond, during condensation of IPP. Furthermore, prenyl diphosphate synthases may catalyze a reaction that further condenses IPP to prenyl diphosphate produced by a condensation reaction. The maximum length of isoprene chain that can be produced by such a condensation polymerization reaction of IPP (the maximum degree of IPP polymerization) is inherent to each prenyl diphosphate synthase. The hydrophobicity of a product changes depending on the isoprene chain length of the product, and, thus, the manner of expression of enzymatic activity significantly varies.

More specifically, prenyl diphosphate synthases can be classified into four types, a prenyl diphosphate synthase I (E-form short-chain prenyl diphosphate synthase), a prenyl diphosphate synthase II (E-form medium-chain prenyl diphosphate synthase), a prenyl diphosphate synthase III (E-form long-chain prenyl diphosphate synthase), and a prenyl diphosphate synthase IV (Z-form long-chain prenyl diphosphate synthase) (Japanese Laid-Open Patent Publication No. 2004-24275).

Examples of the prenyl diphosphate synthase I (E-form short-chain prenyl diphosphate synthase) include a geranyl diphosphate (GPP) synthase (C5→C10), a farnesyl diphosphate (FPP) synthase (C10→C15), and a geranyl geranyl diphosphate (GGPP) synthase (C15→C20). Here, for example, "C5→C10" refers to catalyzing a reaction that produces prenyl diphosphate having ten carbon atoms (C10) by condensing IPP having five carbon atoms to prenyl diphosphate functioning as a primer substrate having five carbon atoms (C5).

Examples of the prenyl diphosphate synthase II (E-form medium-chain prenyl diphosphate synthase) include a hexaprenyl diphosphate (HexPP) synthase (C15→C30) and a heptaprenyl diphosphate (HepPP) synthase (C16→C35).

Examples of the prenyl diphosphate synthase III (E-form long-chain prenyl diphosphate synthase) include an octaprenyl diphosphate (OctPP) synthase (C15→C40), a nonaprenyl diphosphate (NonPP) synthase (C10→C45), and a decaprenyl diphosphate (DecPP) synthase (C15→C50).

Examples of the prenyl diphosphate synthase IV (Z-form long-chain prenyl diphosphate synthase) include a Z-nonaprenyl diphosphate synthase (C15→C45), an undecaprenyl diphosphate (UPP) synthase (C15→C55), and a dehydrodolichyl diphosphate (deDolPP) synthase (C15→C85 to 105).

A rubber transferase gene (HRT2) is isolated from *Hevea brasiliensis*, which is a plant that produces a cis-rubber, and a protein that is encoded by the HRT2 gene is confirmed to have a cis-prenyl diphosphate-synthesizing activity that condenses IPP to rubber particles. Furthermore, the HRT2 gene is confirmed to complement the functional deficiencies of the dehydrodolichyl diphosphate synthases of a budding yeast (K. Asawatreratanakul et al., "molecular cloning, expression and characterization of cDNA encoding cis-prenyltransferases from *Hevea brasiliensis"*, *Eur. J. Biochem.*, 2003, vol. 270, p. 4671-4680). However, it has not been reported that transformation of *Hevea brasiliensis* with an expression vector containing the HRT2 gene results in an increased content of cis-1,4-polyisoprene (cis-rubber) produced by *Hevea brasiliensis*.

On the other hand, genes for long-chain trans-prenyl diphosphate synthases participating in the biosynthesis of a trans-rubber have not been isolated and identified from *Eucommia ulmoides, Periploca sepium, Mimusops balata*, and *Palaquium gutta*, which are plants that produce a trans-rubber. The inventors of the present invention isolated a prenyl transferase gene from *Eucommia ulmoides* (base sequence: GenBank Accession Number AB041626, and amino acid sequence: GenBank Accession Number BAB16687), but have not yet identified whether this gene encodes a cis-prenyl diphosphate synthase or a trans-prenyl diphosphate synthase, and whether this gene encodes a short-chain prenyl diphosphate synthase or a long-chain prenyl diphosphate synthase.

By the way, 3-hydroxy-3-methyl glutaryl coenzyme A reductase (HMGR) is considered to be a key enzyme in the biosynthesis system of IPP functioning as a substrate for prenyl diphosphate synthases. When *Arabidopsis thaliana* is transformed with an expression vector containing DNA that encodes the catalyst domain of the HMGR (HMGR-CD), the transformed *Arabidopsis thaliana* has the total content of sterols that is approximately 3.6 times as large as that of the wild-type (D. Manzano et al., "The metabolic imbalance underlying lesion formation in *Arabidopsis thaliana* overexpressing farnesyl diphosphate synthase (isoform 1S) leads to oxidative stress and is triggered by the developmental decline of endogenous HMGR activity", *Planta*, 2004, vol. 219, p. 982-992). Here, sterols are one of the isoprenoid compounds that are biosynthesized using IPP as a substrate.

For example, coenzyme Q10 is also known as one of the trans-form isoprenoid compounds. Wild-type *Oryza sativa* produces coenzyme Q9 using solanesyl diphosphate (in which nine isoprene units are polymerized) as an intermediate. When *Oryza sativa* is transformed with an expression vector containing DNA that encodes a *Gluconobacter suboxydans*-derived decaprenyl diphosphate (in which ten isoprene units are polymerized) synthase, the transformed *Oryza sativa* does not produce coenzyme Q9, but produces coenzyme Q10 using decaprenyl diphosphate as an intermediate (S. Takahashi et al., "Metabolic engineering of coenzyme Q by modification of isoprenoid side chain in plant", *FEBS Lett.*, 2006, vol. 580, p. 955-959). When *Escherichia coli* is transformed with an expression vector containing DNA that encodes a fungus-derived decaprenyl diphosphate synthase, the transformed *Escherichia coli* effectively produces coenzyme Q10 using decaprenyl diphosphate as an intermediate (International Publication Nos. 2002/092811 and 2002/040682).

SUMMARY OF THE INVENTION

It is an object of the present invention to provide a method for increasing the content of trans-1,4-polyisoprene in a plant, and a method for effectively producing trans-1,4-polyisoprene using a plant.

The inventors of the present invention conducted an in-depth study in order to solve the above-described problems, and found that the content of trans-1,4-polyisoprene in a plant can be increased by isolating and identifying a long-chain trans-prenyl diphosphate synthase gene from *Eucommia ulmoides*, and transforming the plant with an expression vector containing the gene, and trans-1,4-polyisoprene can be effectively produced by means of using the plant, and, thus, the present invention has been achieved.

The present invention provides a long-chain trans-prenyl diphosphate synthase gene comprising at least one of:

(a) DNA having at least one base sequence selected from the group consisting of a base sequence from positions 88 to 1134 of the base sequence of SEQ ID NO: 1 or a complementary sequence thereof, a base sequence from positions 42 to 1088 of the base sequence of SEQ ID NO: 3 or a complementary sequence thereof, and a base sequence from positions 91 to 1140 of the base sequence of SEQ ID NO: 5 or a complementary sequence thereof;

(b) DNA that forms a hybrid with the (a) DNA under stringent conditions and that encodes a protein having long-chain trans-prenyl diphosphate-synthesizing activity;

(c) DNA that encodes a protein having an E-value of $10^{-80}$ or less with respect to at least one amino acid sequence selected from the group consisting of the amino acid sequence of SEQ ID NO: 2, the amino acid sequence of SEQ ID NO: 4, and the amino acid sequence of SEQ ID NO: 6, and having long-chain trans-prenyl diphosphate-synthesizing activity; and (d) DNA that encodes a protein having an amino acid sequence in which one or several amino acids are substituted, added, deleted or inserted in at least one amino acid sequence selected from the group consisting of the amino acid sequence of SEQ ID NO: 2, the amino acid sequence of SEQ ID NO: 4, and the amino acid sequence of SEQ ID NO: 6, and having long-chain trans-prenyl diphosphate-synthesizing activity.

The present invention further provides a long-chain trans-prenyl diphosphate synthase comprising at least one of:

(A) a protein having at least one amino acid sequence selected from the group consisting of the amino acid sequence of SEQ ID NO: 2, the amino acid sequence of SEQ ID NO: 4, and the amino acid sequence of SEQ ID NO: 6;

(B) a protein having an E-value of $10^{-80}$ or less with respect to the amino acid sequence of the (A) protein, and having long-chain trans-prenyl diphosphate-synthesizing activity; and (C) a protein having an amino acid sequence in which one or several amino acids are substituted, added, deleted or inserted in the amino acid sequence of the (A) protein, and having long-chain trans-prenyl diphosphate-synthesizing activity.

The present invention further provides an expression vector containing the long-chain trans-prenyl diphosphate synthase gene.

The present invention further provides a plant transformed with the expression vector.

In one embodiment, the plant is *Eucommia ulmoides*.

In another embodiment, the plant is *Nicotiana tabacum*.

The present invention further provides a method for increasing the amount of trans-1,4-polyisoprene contained in a plant, comprising the step of transforming the plant using the expression vector.

The present invention further provides a method for producing trans-1,4-polyisoprene, comprising the steps of cultivating the plant; and recovering the trans-1,4-polyisoprene from the cultivated plant.

According to the present invention, a plant that has an increase content of trans-1,4-polyisoprene can be provided by transforming the plant with an expression vector containing a long-chain trans-prenyl diphosphate synthase gene. Trans-1,4-polyisoprene can be effectively produced by cultivating such a plant.

DESCRIPTION OF THE PREFERRED EMBODIMENTS

Figure 1:
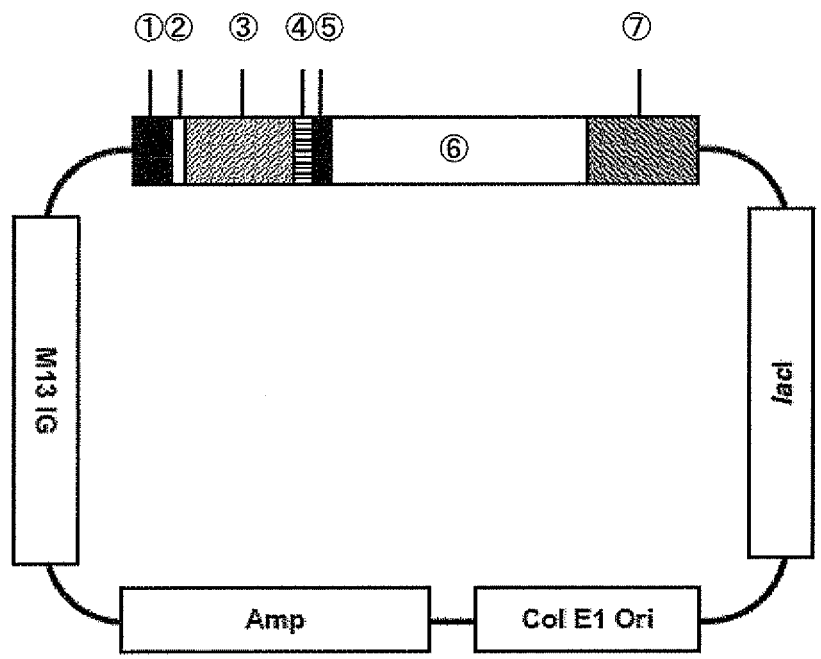
FIG. 1 is a schematic diagram showing the structure of pCold-TPL1, pCold-TPL3 and pCold-TPL5.

The present invention provides a long-chain trans-prenyl diphosphate synthase gene. The long-chain trans-prenyl diphosphate synthase of the present invention is preferably derived from *Eucommia ulmoides*. The long-chain trans-prenyl diphosphate synthase of the present invention has an activity of synthesizing long-chain trans-polyisoprene (trans-1,4-polyisoprene) having a molecular weight of $10^4$ to $10^5$ as substantially described in, for example, Examples 4 to 6 below. The long-chain trans-prenyl diphosphate synthase of the present invention catalyzes the synthesis of trans-prenyl diphosphate, being different from *Hevea brasiliensis*-derived cis-prenyl diphosphate synthase.

The long-chain trans-prenyl diphosphate synthase gene of the present invention may comprise (a) DNA having at least one base sequence selected from the group consisting of a base sequence from positions 88 to 1134 of the base sequence of SEQ ID NO: 1 or a complementary sequence thereof, a base sequence from positions 42 to 1088 of the base sequence of SEQ ID NO: 3 or a complementary sequence thereof, and a base sequence from positions 91 to 1140 of the base sequence of SEQ ID NO: 5 or a complementary sequence thereof.

The long-chain trans-prenyl diphosphate synthase gene of the present invention may comprise (b) DNA that forms a hybrid with the (a) DNA under stringent conditions and that encodes a protein having long-chain trans-prenyl diphosphate-synthesizing activity.

The long-chain trans-prenyl diphosphate synthase gene of the present invention may comprise (c) DNA that encodes a protein having an E-value of $10^{-80}$ or less with respect to at least one amino acid sequence selected from the group consisting of the amino acid sequence of SEQ ID NO: 2, the amino acid sequence of SEQ ID NO: 4, and the amino acid sequence of SEQ ID NO: 6, and having long-chain trans-prenyl diphosphate-synthesizing activity.

The long-chain trans-prenyl diphosphate synthase gene of the present invention may comprise (d) DNA that encodes a protein having an amino acid sequence in which one or several amino acids are substituted, added, deleted or inserted in at least one amino acid sequence selected from the group consisting of the amino acid sequence of SEQ ID NO: 2, the amino acid sequence of SEQ ID NO: 4, and the amino acid sequence of SEQ ID NO: 6, and having long-chain trans-prenyl diphosphate-synthesizing activity.

The gene of the present invention may comprise DNA that forms a hybrid, under stringent conditions, with DNA having at least one base sequence selected from the group consisting of a base sequence from positions 88 to 1134 of the base sequence of SEQ ID NO: 1 or a complementary sequence thereof, a base sequence from positions 42 to 1088 of the base sequence of SEQ ID NO: 3 or a complementary sequence thereof, and a base sequence from positions 91 to 1140 of the base sequence of SEQ ID NO: 5 or a complementary sequence thereof, as long as the gene encodes a protein having the long-chain trans-prenyl diphosphate-synthesizing activity.

The long-chain trans-prenyl diphosphate-synthesizing activity can be confirmed using a method commonly used by those skilled in the art, such as the methods substantially described in, for example, Examples 4 to 6 below.

In the present invention, the stringent conditions refer to the conditions in which only DNA that encodes a protein having the long-chain trans-prenyl diphosphate-synthesizing activity forms a hybrid (a so-called specific hybrid) with DNA that encodes the long-chain trans-prenyl diphosphate synthase, and DNA that encodes a protein not having the synthesizing activity does not form a hybrid (a so-called non-specific hybrid) with DNA that encodes the long-chain trans-prenyl diphosphate synthase. Those skilled in the art can easily determine such conditions by appropriately selecting the salt levels of a reaction liquid and a washing liquid used for forming a hybrid, the temperatures during reaction and washing, and the like. More specifically, the conditions may be applicable in which 6×SSC (0.9M NaCl, 0.09M trisodium citrate) or 6×SSPE (3M NaCl, 0.2M NaH$_2$PO$_4$, 20 mM EDTA-2Na, pH 7.4) is used as a reaction liquid to form a hybrid at 42° C., and then 0.5×SSC is used as a washing liquid to perform washing at 42° C., but there is no limitation to this.

The gene of the present invention may comprise DNA that encodes a protein having an E-value of $10^{-80}$ or less, preferably $10^{-100}$ or less, more preferably $10^{-120}$ or less, even more preferably $10^{-140}$ or less, and even more preferably $10^{-160}$ or less, with respect to an amino acid sequence of a protein having at least one amino acid sequence selected from the group consisting of the amino acid sequence of SEQ ID NO: 2, the amino acid sequence of SEQ ID NO: 4, and the amino acid sequence of SEQ ID NO: 6, as long as the gene encodes a protein having the long-chain trans-prenyl diphosphate-synthesizing activity.

In the present invention, the E-value refers to an expected value that is an index of homology, that is, an expected value of the number of homologous sequences that are found completely accidentally in a database. In the NCBI homology search program BLAST, the E-value refers to a value of a comparison result (Expect) displayed for one of two sequences that are to be compared when the other sequence is input as a query sequence using default parameters. A smaller E-value indicates a higher homology.

The gene of the present invention may comprise DNA that encodes a protein having an amino acid sequence in which one or several (20 or less, preferably ten or less, more preferably five or less, and even more preferably three or less) amino acids are substituted, added, deleted or inserted in an amino acid sequence of the long-chain trans-prenyl diphosphate synthase, as long as the gene encodes a protein having the long-chain trans-prenyl diphosphate-synthesizing activity. Such a mutation of the amino acid sequence may result from substitution, addition, deletion or insertion of a base on the DNA, and may result from either natural induction of mutation or artificial induction of mutation (e.g., use of a site-directed mutagenesis).

The gene of the present invention can be obtained by preparing a probe or a primer based on the sequence information described in this specification and performing PCR that uses the chromosome DNA or cDNA of *Eucommia ulmoides* as a template, using a method commonly used by those skilled in the art. It will be appreciated that the gene of the present invention can also be obtained via reverse transcription-PCR that uses RNA as a template. The gene of the present invention may be not only natural polynucleotides of DNA, RNA or the like, but also artificial molecules containing artificial nucleotide derivatives. Furthermore, the gene of the present invention may also be a chimera molecule of DNA-RNA.

The long-chain trans-prenyl diphosphate synthase of the present invention may comprise (A) a protein having at least one amino acid sequence selected from the group consisting of the amino acid sequence of SEQ ID NO: 2, the amino acid sequence of SEQ ID NO: 4, and the amino acid sequence of SEQ ID NO: 6.

The long-chain trans-prenyl diphosphate synthase of the present invention may comprise (B) a protein having an E-value of $10^{-80}$ or less with respect to the amino acid sequence of the (A) protein, and having long-chain trans-prenyl diphosphate-synthesizing activity.

The long-chain trans-prenyl diphosphate synthase of the present invention may comprise (C) a protein having an amino acid sequence in which one or several amino acids are substituted, added, deleted or inserted in the amino acid sequence of the (A), and having long-chain trans-prenyl diphosphate-synthesizing activity.

The enzyme of the present invention may comprise a protein having an E-value of $10^{-80}$ or less, preferably $10^{-100}$ or less, more preferably $10^{-120}$ or less, even more preferably $10^{-140}$ or less, and even more preferably $10^{-160}$ or less, with respect to an amino acid sequence of a protein having at least one amino acid sequence selected from the group consisting of the amino acid sequence of SEQ ID NO: 2, the amino acid sequence of SEQ ID NO: 4, and the amino acid sequence of SEQ ID NO: 6, as long as the enzyme has the long-chain trans-prenyl diphosphate-synthesizing activity.

The enzyme of the present invention may comprise a protein having an amino acid sequence in which one or several (20 or less, preferably ten or less, more preferably five or less, and even more preferably three or less) amino acids are substituted, added, deleted or inserted in an amino acid sequence of a protein having at least one amino acid sequence selected from the group consisting of the amino acid sequence of SEQ ID NO: 2, the amino acid sequence of SEQ ID NO: 4, and the amino acid sequence of SEQ ID NO: 6, as long as the enzyme has the long-chain trans-prenyl diphosphate-synthesizing activity.

The enzyme of the present invention taxonomically belongs to transferase (EC2.5.1), and is classified as the long-chain prenyl diphosphate synthase III (E-form long-chain prenyl diphosphate synthase). The enzyme of the present invention catalyzes a condensation reaction that uses prenyl diphosphate (C5n) having 5n carbon atoms (n is an integer) and isopentenyl diphosphate (IPP, C5) having five carbon atoms as a substrate and transfers an isoprenyl group (C5) to the prenyl diphosphate (C5n), thereby producing prenyl diphosphate (C5(n+1)) having 5(n+1) carbon atoms and a by-product of diphosphate. This condensation reaction is characterized in that the isoprenyl group is transferred to the prenyl diphosphate (C5n) at the trans-position. The maximum number of isoprene units (isoprene chain length) or the maximum degree of IPP polymerization that can be produced by a condensation polymerization reaction that repeats the condensation reaction is 11 or more, preferably 20 or more, more preferably 30 or more, and even more preferably 40 or more. The enzyme of the present invention can be purified according to a common method, and can be purified according to, for example, the method described in Example 4 below.

The enzyme of the present invention has high homology (E-value <$10^{-80}$) with an FPP synthase of an eukaryote on the amino acid sequence. The amino acid sequence of a prenyl diphosphate synthase of an eukaryote has two aspartate-rich motifs (first aspartate-rich motif (FARM) and second aspartate-rich motif (SARM)). In the enzyme of the present invention, the FARM sequence refers to an amino acid sequence comprising aspartic acid-aspartic acid-isoleucine-methionine seen in, for example, an amino acid sequence from positions 99 to 102 of the amino acid sequence of SEQ ID NO: 2, an amino acid sequence from positions 99 to 102 of the amino acid sequence of SEQ ID NO: 4, or an amino acid sequence from positions 100 to 103 of the amino acid sequence of SEQ ID NO: 6. In the amino acid sequence of an FPP synthase of an eukaryote, an amino acid sequence consisting of tyrosine immediately followed by phenylalanine, or an amino acid sequence consisting of phenylalanine immediately followed by phenylalanine is present near the amino terminal end of the FARM. These amino acid sequences are considered to participate in the degree of IPP polymerization in the condensation polymerization reaction catalyzed by a prenyl diphosphate synthase. In the enzyme of the present invention, these amino acid sequences are replaced by an amino acid sequence consisting of cysteine immediately followed by alanine. It seems that this substitution provides the enzyme of the present invention with a long-chain prenyl diphosphate-synthesizing activity.

Accordingly, the gene of the present invention may comprise DNA that encodes an amino acid sequence consisting of cysteine immediately followed by alanine near the amino terminal end of the FARM in the amino acid sequence, for example, DNA having a base sequence from positions 367 to 372 of the base sequence of SEQ ID NO: 1, a base sequence from positions 321 to 326 of the base sequence of SEQ ID NO: 3, or a base sequence from positions 373 to 378 of the base sequence of SEQ ID NO: 5, as long as the gene encodes a protein having the long-chain trans-prenyl diphosphate-synthesizing activity.

Furthermore, the enzyme of the present invention may comprise a protein having an amino acid sequence consisting of cysteine immediately followed by alanine near the amino terminal end of the FARM in the amino acid sequence, for example, an amino acid sequence from positions 94 to 95 of the amino acid sequence of SEQ ID NO: 2, an amino acid sequence from positions 94 to 95 of the amino acid sequence of SEQ ID NO: 4, or an amino acid sequence from positions 95 to 96 of the amino acid sequence of SEQ ID NO: 6, as long as the enzyme has the long-chain trans-prenyl diphosphate-synthesizing activity.

Furthermore, the enzyme of the present invention has an insertion sequence of 6 amino acids that is not present in an FPP synthase of an eukaryote, between the amino terminal end and the FARM of the amino acid sequence. Analysis of an expected three-dimensional structural model suggests that this insertion sequence forms a protruding structure on the surface of a protein, and this insertion sequence may function as a localization signal.

Accordingly, the gene of the present invention may comprise DNA that encodes an insertion sequence of 6 amino acids that is not present in the FPP synthase, between the amino terminal end and the FARM of the amino acid sequence, for example, DNA having a base sequence from positions 277 to 294 of the base sequence of SEQ ID NO: 1, a base sequence from positions 231 to 248 of the base sequence of SEQ ID NO: 3, or a base sequence from positions 283 to 300 of the base sequence of SEQ ID NO: 5, as long as the gene encodes a protein having the long-chain trans-prenyl diphosphate-synthesizing activity.

Furthermore, the enzyme of the present invention may comprise a protein having an insertion sequence of 6 amino acids that is not present in the FPP synthase, between the amino terminal end and the FARM of the amino acid sequence, for example, an amino acid sequence from positions 64 to 69 of the amino acid sequence of SEQ ID NO: 2, an amino acid sequence from positions 64 to 69 of the amino acid sequence of SEQ ID NO: 4, or an amino acid sequence from positions 65 to 70 of the amino acid sequence of SEQ ID NO: 6, as long as the enzyme has the long-chain trans-prenyl diphosphate-synthesizing activity.

The expression vector of the present invention includes the long-chain trans-prenyl diphosphate synthase gene. The expression vector of the present invention can be constructed using a method commonly used by those skilled in the art. Various base vectors can be used depending on a host that is to be transformed. For example, in the case of *Escherichia coli*, examples of the vector include pUC19, pMAL-p2, pCold I, pGEX, pET, pMalc2, pTrc99A, and the like. In the case of a yeast, examples of the vector include pYES, pYC, pYI, pYL, pYEUra3TM, and the like. In the case of a plant, examples of the vector include pIG121-Hm, pBI12, pBI221, pBIN19, pCAMBIA2301, pCC22, pGA482, pPCV001, pCGN1647, pJJ1881, pPZP111, pGreen0029, pBI101, pBI121, pYLTAC7, and the like. The vectors appropriately include not only a target gene, but also DNA participating in the regulation of gene expression, such as a promoter and a terminator for expressing the gene, and a selection marker for selecting a transformant. Various promoters can be used depending on a host that is to be transformed. For example, in the case of *Escherichia coli*, examples of the promoter include T7 promoter, lac promoter, tac promoter, trp promoter, cspA promoter, and the like. In the case of a yeast, examples of the promoter include PMA1 promoter, ADH1 promoter, GAL1 promoter, PGK promoter, PHO5 promoter, GAPDH promoter, and the like. In the case of a plant, examples of the promoter include CaMV35S promoter, NOS promoter, CAB promoter, UBI promoter, and the like.

In the present invention, examples of the host that is to be transformed include microorganisms, such as *Escherichia coli* and yeasts, and plants. The host is preferably a plant, and more preferably *Eucommia ulmoides* belonging to the family Eucommiaceae and *Periploca sepium* belonging to the family Apocynaceae. Various transformation methods can be used depending on the host that is to be transformed. For example, in the case of *Escherichia coli*, examples of the method include competent cell methods, electroporation methods, and the like. In the case of a yeast, examples of the method include lithium acetate methods, spheroplast methods, and the like. In the case of a plant, examples of the method include Agrobacterium methods, particle gun bombardment methods, electroporation methods, and the like. The transformant can be selected and separated from wild-type, which have not been transformed, by using a selection marker contained in the vector. Examples of the selection marker that can be commonly used include an antibiotic resistance gene, a green fluorescent protein (GFP) gene, and the like, and various selection markers can be used depending on the host that is to be transformed. For example, in the case of *Escherichia coli*, examples of the selection marker include an ampicillin resistance gene, a chloramphenicol resistance gene, and the like. In the case of a yeast, examples of the selection marker include an aureobasidin A resistance gene and a gene for a nutritional auxotrophy such as various amino acid auxotrophies, and the like. In the case of a plant, examples of the selection marker include a kanamycin resistance gene, a hygromycin resistance gene, and the like.

In order to produce a transformed plant (e.g., *Eucommia ulmoides, Periploca sepium, Nicotiana tabacum*, and the like, preferably *Eucommia ulmoides*) that has an increased content of trans-1,4-polyisoprene, the long-chain trans-prenyl diphosphate synthase gene of the present invention can be preferably used for transforming the plant.

The transformed plant (preferably transformed *Eucommia ulmoides*) of the present invention can be cultivated using a method commonly used by those skilled in the art. The trans-1,4-polyisoprene can be recovered and purified using a method commonly used by those skilled in the art from leaves, bark, peel, and the like of a mature tree of the transformed *Eucommia ulmoides*.

EXAMPLES

Hereinafter, the present invention will be described further in detail by way of examples, but the present invention is not limited thereto.

Example 1

Isolation of TPL1-cDNA (SEQ ID NO: 1)

Preparation of the Total RNA of *Eucommia ulmoides*: 1

Leaves of a young current year's branch collected in late May from an *Eucommia ulmoides* sample tree grown in Ikina, Ehime (Japan) were used as an *Eucommia ulmoides* plant body sample. While being cooled with liquid nitrogen, the *Eucommia ulmoides* plant body sample (the leaves of the current year's branch) was crushed with a mortar and pestle, and suspended in 2×CTAB solution (2% (w/v) hexadecyltrimethylammonium bromide (CTAB), 1% (w/v) β-mercaptoethanol, 0.1M Tris-HCl (pH 9.5), 1.4M NaCl, and 20 mM EDTA) with a volume ten times (w/v) the sample. The resultant was incubated at 65° C. for ten minutes, and then treated (washed) with chloroform/isoamyl alcohol (repeated twice). Subsequently, to the recovered aqueous layer, 10M LiCl with a volume ¼ times (w/v) the aqueous layer was added, and the mixture was allowed to stand at −20° C. for two hours, thereby performing RNA-selective precipitation. The resultant was centrifuged, the precipitate was dissolved in an appropriate volume of tris-EDTA (TE) buffer solution, subsequently the resultant was centrifuged, and the supernatant was recovered, while polysaccharides were removed. The recovered supernatant was treated with phenol, phenol/chloroform, and chloroform/isoamyl alcohol, and RNA-selective precipitation with LiCl was performed again. The precipitate was washed with 70% ethanol, dried under reduced pressure, and then dissolved in diethylpyrocarbonate (DEPC)-treated water to give the total RNA.

Preparation of *Eucommia ulmoides*-Derived cDNA

A reverse transcription reaction was performed using the *Eucommia ulmoides* leaf-derived total RNA as a template, and AMV Reverse Transcriptase XL (manufactured by Takara Bio Inc.) to give *Eucommia ulmoides*-derived cDNA. Oligo dT Adaptor Primer (manufactured by Takara Bio Inc.) was used as a primer for the reverse transcription reaction.

Determination of TPL1-cDNA Partial Sequence Using Degenerate PCR

A first PCR was performed using the *Eucommia ulmoides*-derived cDNA as a template, and TaKaRa Ex Taq (manufactured by Takara Bio Inc.). Next, a second PCR was performed using the first PCR product as a template, and TaKaRa Ex Taq. In both PCRs, degenerate primers were used as primers, and the base sequences were as follows. In both PCRs, a cycle of five minutes at 94° C. was performed once, a cycle of one minute at 94° C., one minute at 54° C. and then two minutes at 74° C. was performed 30 times, and then a cycle of seven minutes at 74° C. was performed once. The amplified fragments obtained by the second PCR were cloned into the pUC18 vector, and sequenced for a plurality of the plasmid clones. As a result, it was found that some of the clones had a partial sequence of the base sequence of SEQ ID NO: 1.

Primer Set for the First PCR

```
Sense      CIYTIGGITGGTGYRTNGARTGG    (SEQ ID NO: 7)
primer:

Antisense  GTYCANGTYCTRCTIATIIAICTIAC (SEQ ID NO: 8)
primer:
```

Primer Set for the Second PCR

```
Sense      GGTGIRTIGARTGGYTNCARGC     (SEQ ID NO: 9)
primer:

Antisense  CCCNTRNATRAAIGTICAIGTIC    (SEQ ID NO: 10)
primer:
```

Preparation of the Total RNA of *Eucommia ulmoides*: 2

Total RNA was prepared as in the preparation of the total RNA of *Eucommia ulmoides* 1, excerpt that phloem (bark) and xylem of a young current year's branch collected in late May from an *Eucommia ulmoides* sample tree grown in Ikina, Ehime (Japan) were used as an *Eucommia ulmoides* plant body sample. The obtained total RNA was quantified by measuring optical density (OD), and confirmed by electrophoresis. Here, 2 mg of total RNA was obtained from approximately 4 g of phloem, and 0.84 mg of total RNA was obtained from approximately 4 g of xylem (the ratios of OD at 260 nm to OD at 280 nm were 1.991 and 1.956, respectively).

Preparation of cDNA Library of *Eucommia ulmoides*

Then, mRNA was purified from the *Eucommia ulmoides* phloem and xylem-derived total RNA sample using Oligotex-dT30<Super> (manufactured by Takara Bio Inc.). Next, a cDNA library was prepared from the mRNA using the Lambda ZAP II XR Library Construction Kit (manufactured by Stratagene).

Preparation of Probe for cDNA Library Screening

PCR was performed using the plasmid clones obtained in the degenerate PCR and containing a partial sequence of the base sequence of SEQ ID NO: 1 as a template, and TaKaRa Ex Taq. The base sequences of the primers used were as follows. In the PCR, a cycle of five minutes at 94° C. was performed once, a cycle of one minute at 94° C., one minute at 50° C. and then one minute at 72° C. was performed 30 times, and then a cycle of seven minutes at 72° C. was performed once. The PCR reaction product was labeled with alkaline phosphatase using AlkPhos Direct Labelling and Detection System with CDP-Star (manufactured by GE Healthcare) to give a probe for screening.

Primer Set for PCR

```
Sense primer: GTGCTCTTGTTCTTGATGATA (SEQ ID NO: 11)

Antisense     CAAGAAGTATGTCCTTCATGT (SEQ ID NO: 12)
primer:
```

Screening of *Eucommia ulmoides* cDNA Library

From the *Eucommia ulmoides* cDNA library, phage plaque lifting was performed onto an Hybond N+ membrane (manufactured by GE Healthcare) according to a common method. Next, this membrane was subjected to hybridization, washing and signal detection using the probe for screening and the AlkPhos Direct Labelling and Detection System with CDP-Star. The hybridization was performed at 55° C. for 16 hours, primary washing was performed twice at 55° C. for ten minutes, and secondary washing was performed twice at room temperature for five minutes. As a result of the screening, it was found that 23 positive phage plaques were obtained. Next, these phage clones were converted to plasmid clones by in vivo excision using the Lambda ZAP II XR Library Construction Kit. The 23 plasmid clones were sequenced. As a result, it was found that ten clones had the same base sequence as the base sequence of SEQ ID NO: 1 or a base sequence considered to be a splicing variant thereof.

Example 2

Isolation of TPL3-cDNA (SEQ ID NO: 3)

TPL3-cDNA was isolated as in Example 1. The obtained full-length cDNA (TPL3-cDNA) had the base sequence of SEQ ID NO: 3. The base sequence from positions 37 to 1089 of the base sequence of SEQ ID NO: 3 had a homology of 76% with the base sequence of TPL1-cDNA (SEQ ID NO: 1: GenBank Accession Number AB041626). The base sequence from positions 42 to 1088 of the base sequence of SEQ ID NO: 3 had an open reading frame. The deduced amino acid sequence encoded by this cDNA is as shown in SEQ ID NO: 4. The complete amino acid sequence (positions 1 to 348) of SEQ ID NO: 4 has an E-value of $10^{-169}$ (a homology of 77%) with respect to the amino acid sequence of TPL1 (SEQ ID NO: 2: GenBank Accession Number BAB16687).

Example 3

Isolation of TPL5-cDNA (SEQ ID NO: 5)

Preparation of cDNA Library of *Eucommia ulmoides*

From an *Eucommia ulmoides* phloem and xylem-derived total RNA sample prepared as in Example 1, a cDNA library was prepared by the G-capping method at Hitachi Instruments Service Co., Ltd. The phloem-derived cDNA library had a library size of $3.8 \times 10^5$, an insertion ratio of 88% (24 samples/agarose gel electrophoresis), and a full-length ratio of 86% (with respect to clones carrying inserts). The xylem-derived cDNA library had a library size of 2.2×10⁵, an insertion ratio of 79% (24 samples/agarose gel electrophoresis), and a full-length ratio of 63% (with respect to clones carrying inserts).

EST Analysis of *Eucommia ulmoides*

Approximately 20000 clones of each of the *Eucommia ulmoides* phloem and xylem-derived cDNA libraries were subjected to base sequence analysis at the Laboratory of Genome Informatics of the Kitasato Institute for Life Sciences, Kitasato University. Based on the sequence information obtained by the sequence analysis, clones not carrying inserts and clones for which the sequence could not be read were removed, and precise sequence information was obtained. Here, 16567 and 16113 precise EST sequences were obtained for the phloem and xylem libraries (total 32680), respectively. Next, the obtained sequences were subjected to clustering and annotation. "Clustering" refers to processing that clusters the same sequences and similar sequences among the EST sequences. NTT software VISUALBIO clustering was used for the clustering. "Annotation" refers to processing that annotates the EST sequences based on comparison with known genes. A homology search using NCBI BLAST was used for the annotation. The database used for the search was nr (All non-redundant GenBank CDS translations+PDB+SwissProt+PIR (Peptide Sequence Database)).

Isolation of TPL5-cDNA

Based on the information obtained by the clustering and the annotation, a sequence on the 5'-terminal end side of TPL5 (SEQ ID NO: 5) having an extremely high homology with TPL1 (SEQ ID NO: 1) was found. A sequence on the 3'-terminal end side of TPL5 (SEQ ID NO: 5) was determined by 3'-RACE (Rapid Amplification of cDNA Ends, RACE). Here, a 3'-Full RACE Core Set (manufactured by Takara Bio Inc.) was used for the 3'-RACE. First, a reverse transcription reaction was performed using the total RNA obtained in Example 1 as a template, and Oligo dT-3 sites Adaptor Primer attached to the 3'-Full RACE Core Set as a primer. Next, a first PCR was performed using the reverse transcription reaction product as a template, and, then, a second PCR was performed using the first PCR product as a template. The base sequences of the primers used were as follows. In both of the first and the second PCRs, a cycle of 60 seconds at 94° C., 60 seconds at 54° C. and then two minutes at 74° C. was performed 30 times. The amplified fragments obtained by the second PCR were TA cloned into the pT7Blue vector (manufactured by Takara Bio Inc.), and sequenced.

Primer Set for the First PCR

Sense primer: ACAGTGGCTGGGCAGATGATAG (SEQ ID NO: 13)

Antisense primer: 3 sites Adaptor Primer attached to the 3'-Full RACE Core Set

Primer Set for the Second PCR

Sense primer: TTACCACACTTCTCGGAGAGGC (SEQ ID NO: 14)

Antisense primer: CGCTTGCATCCATTCGATACACC (SEQ ID NO: 15)

The obtained full-length cDNA (TPL5-cDNA) had the base sequence of SEQ ID NO: 5. The base sequence from positions 113 to 1132 of the base sequence of SEQ ID NO: 5 had a homology of 76% with the base sequence of TPL1-cDNA (SEQ ID NO: 1: GenBank Accession Number AB041626). The base sequence from positions 91 to 1140 of the base sequence of SEQ ID NO: 5 had an open reading frame. The deduced amino acid sequence encoded by this cDNA is as shown in SEQ ID NO: 6. The complete amino acid sequence (positions 1 to 349) of SEQ ID NO: 6 has an E-value of $10^{-166}$ (a homology of 79%) with respect to the amino acid sequence of TPL1 (SEQ ID NO: 2: GenBank Accession Number BAB16687).

Example 4

Preparation and Analysis of TPL Protein

Construction of TPL Expression Vector

Total RNA was prepared from leaves of the *Eucommia ulmoides* sample tree using an RNeasy Plant Mini Kit (manufactured by Qiagen). Buffer RLC provided with the kit was used as a buffer solution for total RNA extraction. Next, cDNA fragments of TPL1, TPL3 and TPL5 were amplified by PCR using the total RNA as a template, and a High Fidelity RNA PCR Kit (manufactured by Takara Bio Inc.). The base sequences of the primers used were as follows. In the PCR, a cycle of 30 seconds at 94° C., 30 seconds at 55° C. and then two minutes at 72° C. was performed 35 times.

Primer Set for TPL1-cDNA Amplification

Sense primer: ACGCTGTCCTTGCACTTG (SEQ ID NO: 16)

Antisense primer: GGAGAACCAAATATGCAATAAAGCCTG (SEQ ID NO: 17)

Primer Set for TPL3-cDNA Amplification

Sense primer: GGCCTTTCGTTCTCTCTCTCTCTCTT (SEQ ID NO: 18)

Antisense primer: ACGACTACATTTATTCAGGTTCGAAGTC (SEQ ID NO: 19)

Primer Set for TPL5-cDNA Amplification

Sense primer: GATCAACACATCCTTGAGCGTTACC (SEQ ID NO: 20)

Antisense primer: GTTAGTCGTTGCAATTTATTTGTTCCCTC (SEQ ID NO: 21)

Each amplified fragment obtained by the PCR was inserted into the restriction enzyme EcoRV site in the multicloning site of plasmid pBluescript II KS—(manufactured by Stratagene), and plasmid clones were constructed. The plasmid clones into which the cDNA of TPL1, TPL3 and TPL5 was inserted were designated as pBluescript-TPL1, pBluescript-TPL3 and pBluescript-TPL5, respectively. Each clone was sequenced and confirmed to have no mutation due to PCR amplification.

Fragments of the sequence encoding the protein of TPL1, TPL3 and TPL5 were amplified by PCR using each plasmid clone as a template, and Pyrobest DNA Polymerase (manufactured by Takara Bio Inc.). The base sequences of the primers used were as follows. The sense primer had a recognition sequence of the restriction enzyme NdeI at the 5'-terminal end, and the antisense primer had a recognition sequence of the restriction enzyme XhoI at the 5'-terminal end. In the PCR, a cycle of 30 seconds at 94° C., 30 seconds at 55° C. and then two minutes at 72° C. was performed 35 times.

Primer Set for Amplification of TPL1 Protein-Encoding Sequence

```
                                      (SEQ ID NO: 22)
Sense primer: GAGAGAGCATATGGCGGAACTGAAGAAAGAATTTC (SEQ ID NO: 23)
Antisense:    CCGCTCGAGCTACTTGAGCCTCCTGTGAATCTTAG
primer:
```

Primer Set for Amplification of TPL3 Protein-Encoding Sequence

```
                                      (SEQ ID NO: 24)
Sense primer: GAGAGAGCATATGACCGAGCTGAAGAGCAAATTTG (SEQ ID NO: 25)
Antisense    CCGCTCGAGCTACTTGAGCCTCTTGTGTATCTTAGC
primer:
```

Primer Set for Amplification of TPL5 Protein-Encoding Sequence

```
                                      (SEQ ID NO: 26)
Sense primer: GAGAGAGCATATGGCGGAAACGACCCAA (SEQ ID NO: 27)
Antisense    CCGCTCGAGTCAATAATGCCTCCGATAGATCTTTGC
primer:
```

Each amplified fragment obtained by the PCR was inserted between the restriction enzyme NdeI site and the restriction enzyme XhoI site in the multicloning site of the cold shock expression vector pCold I (manufactured by Takara Bio Inc.), and TPL expression vectors were constructed. pCold I has a structure in which a protein that is expressed by a gene inserted into the multicloning site and a histidine hexamer tag (His-Tag) can be produced as a fusion protein. The TPL expression vectors into which fragments of the sequence encoding the protein of TPL1, TPL3 and TPL5 were inserted were designated as pCold-TPL1, pCold-TPL3 and pCold-TPL5 (FIG. 1), respectively. Each vector was sequenced and confirmed to have no mutation due to PCR amplification.

Transformation of *Escherichia coli*

In order to express the TPL protein as a soluble protein inside an *Escherichia coli* cell, first, a competent cell of an *Escherichia coli* BL21 (DE3) strain was transformed with chaperone plasmid pG-Tf2 (manufactured by Takara Bio Inc.). Next, from the transformed *Escherichia coli* obtained a competent cell was further prepared, and this competent cell was transformed with TPL expression vector pCold-TPL1, pCold-TPL3 or pCold-TPL5. In this manner, transformed *Escherichia coli* in which a TPL expression vector and a chaperone plasmid coexpressed was obtained.

Preparation of TPL Protein

The coexpressing transformed *Escherichia coli* was cultured with shaking at 37° C. in 50 mL of LB medium containing ampicillin (50 μg/mL) and chloramphenicol (20 μg/mL), which are agents for selecting transformants, and tetracycline (1 ng/mL), which is an agent for inducing chaperone expression, until OD at 600 nm of the culture medium was approximately 0.5 (before induction of expression). Next, the culture medium was cooled at 15° C. for 30 minutes, and isopropyl-β-D-thiogalactoside (final concentration 0.5 mM) was added thereto. Next, culturing with shaking was continued at 15° C. for another 24 hours (after induction of expression).

*Escherichia coli* was recovered by centrifugation from 10 mL of the culture medium after induction of expression, and suspended in 1 mL of cell-crushing buffer solution (60 mM $NaH_2PO_4$, 300 mM NaCl, 10 mM imidazole, 0.5 mM PMSF, 2% TritonX100, 1 mg/mL lysozyme, pH 8.0). After the suspension was allowed to stand on ice for ten minutes, *Escherichia coli* in the suspension was crushed on ice using an ultrasonic crusher SONIFIER450 (manufactured by Branson), and then the liquid after crushing was separated into supernatant and precipitate by centrifugation at 10000×g at 4° C. for 30 minutes. A TPL protein fused with a histidine hexamer tag produced was purified from the supernatant using an Ni-NTA spin column (manufactured by Qiagen) under non-denaturing conditions. A washing buffer solution (50 mM $NaH_2PO_4$, 300 mM NaCl, 50 mM imidazole, 0.1% TritonX100, pH 8.0) was used to wash the column, and an elution buffer solution (50 mM $NaH_2PO_4$, 300 mM NaCl, 500 mM imidazole, 0.1% TritonX100, pH 8.0) was used to elute the TPL protein.

Analysis of TPL Protein

Figure 2:
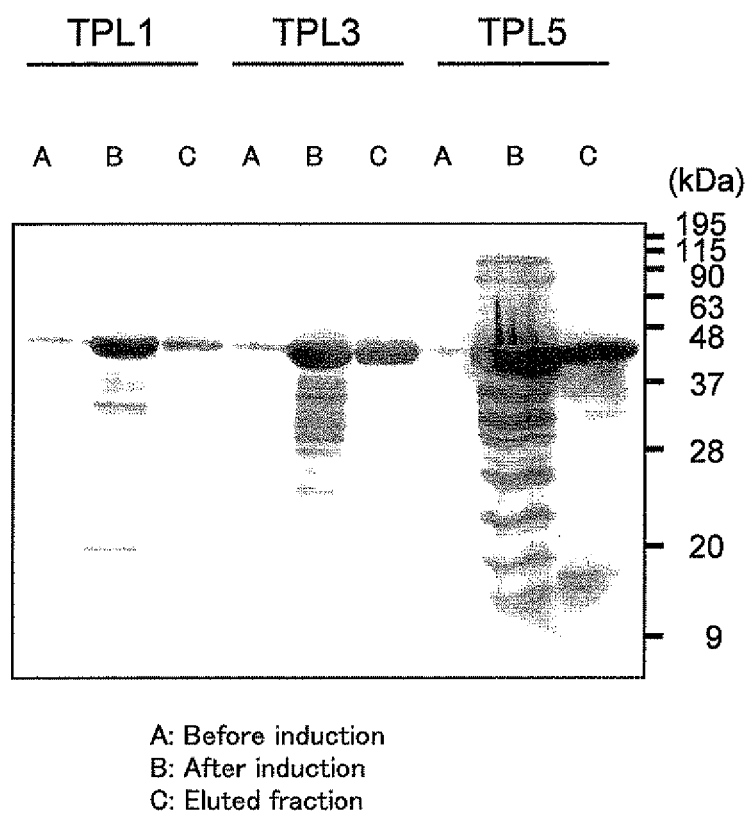
FIG. 2 is an electrophoretogram showing the results of SDS-PAGE and Western blotting of TPL proteins.

Samples taken during preparation of the TPL protein were analyzed by SDS-PAGE and Western blotting. In the SDS-PAGE, 0.05 mM. Tris-HCl (pH 6.8) containing 2% SDS and 6% β-mercaptoethanol was used as a buffer solution for the gel, a buffer solution for electrophoresis and a buffer solution for samples, and the acrylamide concentration in the separation gel was 10%. The culture medium before induction of expression and the culture medium after induction of expression, and eluted fractions of the TPL proteins were heated in a buffer solution for samples at 100° C. for five minutes, and each 10 μL was subjected to SDS-PAGE. In the Western blotting, transfer was performed from the gel-after SDS-PAGE onto a Hybond-P PVDF membrane (manufactured by GE Healthcare), and this membrane was reacted with His-Tag Monoclonal Antibody (manufactured by Novagen) diluted 1000 times as a primary antibody, and then with Anti-Mouse IgG (H+L) AP Conjugate (manufactured by Promega) diluted 5000 times as a secondary antibody. Using the ProtoBlot II AP System with Stabilized Substrate (manufactured by Promega), signals on the membrane were detected. FIG. 2 shows the results. FIG. 2 shows that the TPL proteins were purified.

Figure 3:
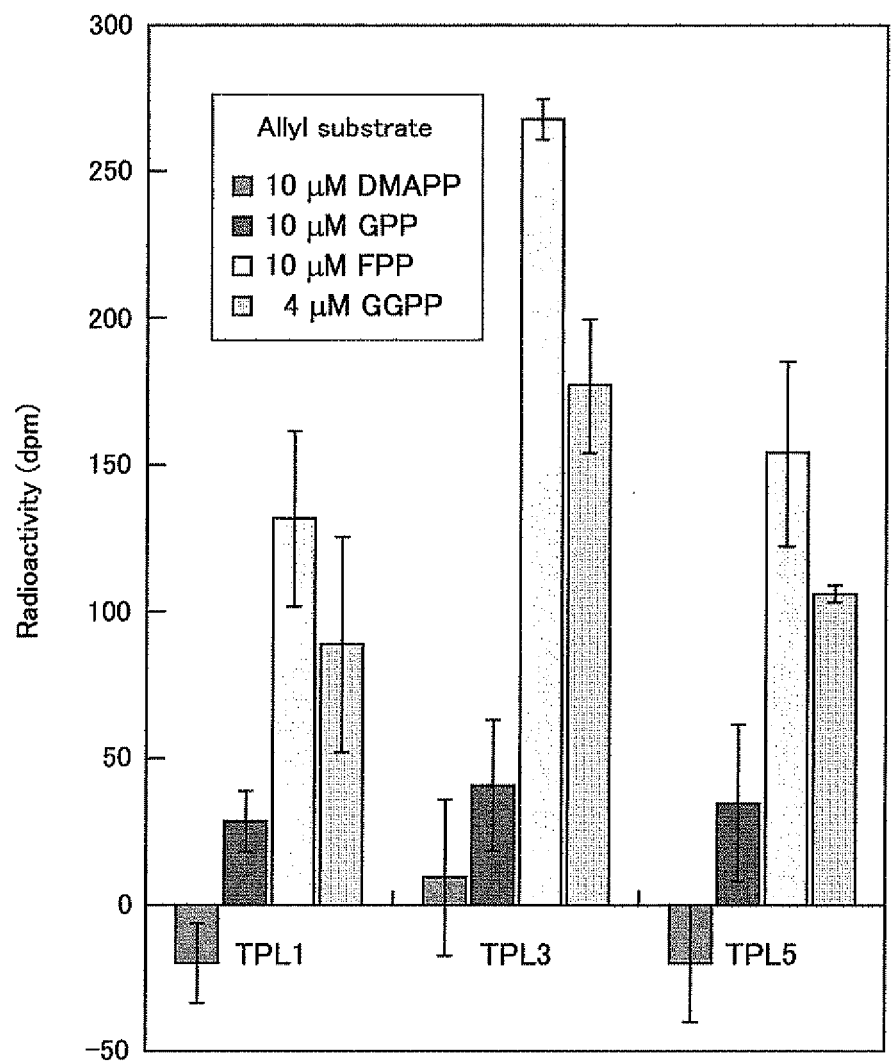
FIG. 3 is a graph showing the prenyl diphosphate-synthesizing activity of TPL proteins.

Next, the prenyl diphosphate-synthesizing activity of the purified TPL proteins was measured. First, 200 μL of enzyme reaction liquid containing 5% of an eluted fraction of the TPL protein (sample), 10 μM or 4 μM of allyl substrate, and 100 μM of radioactive $^{32}$P-labeled IPP (37 GBq/mol) in a buffer solution (100 mM K-MOPS (pH 8.0), 5 mM $MgCl_2$, 0.1% TritonX100) was prepared, and allowed to stand at 30° C. for 16 hours. Next, 200 μL of NaCl-saturated water and 1 mL of butanol saturated with NaCl-saturated water were added to the enzyme reaction liquid, and the mixture was vigorously vortexed for one minute, and, thus, the enzyme reaction was stopped. The resultant was centrifuged at room temperature for three minutes, and separated into an aqueous layer and a butanol layer. Next, 200 μL of the butanol layer was mixed with 3 mL of a liquid scintillation cocktail Clear-sol I (manufactured by Nacalai Tesque, Inc.), and the radioactivity (dpm) of the mixed liquid was measured in a liquid scintillation counter Tri-Carb 2100 (manufactured by Packard). IPP is insoluble in butanol, but a reaction product of IPP and an allyl substrate is soluble in butanol. Thus, the radioactivity of the butanol layer indicates the IPP condensation polymerization reaction activity due to a prenyl diphosphate synthase. FIG. 3 shows the results. FIG. 3 shows, for each sample, the average (bar graph) and standard deviation (error bar) of the values obtained from triplicated experiments by subtracting the radioactivity of an enzyme reaction liquid without a sample (background) from the radioactivity of the enzyme reaction liquid with a sample. It is apparent from FIG. 3 that all of TPL1, TPL3 and TPL5 catalyze an IPP polymerization reaction when using FPP or GGPP as an allyl substrate. However, the IPP polymerization reaction was not catalyzed when using DMAPP (dimethylallyl pyrophosphate) as an allyl substrate.

Example 5

Transformation of *Eucommia ulmoides* Cultured Root

Construction of Plant-Transforming TPL Expression Vector

Figure 4:
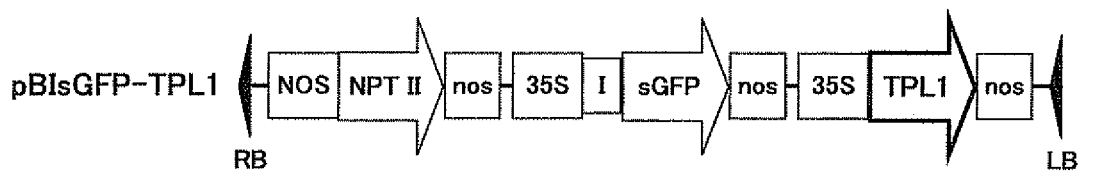
FIG. 4 is a schematic diagram showing the structure of plant-transforming TPL expression vector pBIsGFP-TPL1.

Restriction enzyme NdeI-XhoI fragments of the TPL expression vector pCold-TPL1 were inserted between the restriction enzyme XhoI site and the restriction enzyme KpnI site in the multicloning site of the plant-transforming vector pBIsGFP (given by Norihiro Mitsukawa, Biotechnology Division, Toyota Central R&D Labs, Inc.), and a plant-transforming TPL expression vector pBIsGFP-TPL1 was constructed (FIG. 4). The pBIsGFP contains a kanamycin resistance gene and a modified GFP gene.

Transformation of *Eucommia ulmoides* Cultured Root

Seeds collected from a female strain of *Eucommia ulmoides* grown in Chengdu, Sichuan Province, China were aseptically disseminated in a germination medium (½ MS medium, 20 g/L sucrose). A rootlet of a young plant body at 10 to 20 days after dissemination was excised into pieces having a length of 2 to 3 cm, and cultured with reciprocal shaking (120 revolution/min) in a growth medium (½ MS liquid medium, 1 µM NAA). This *Eucommia ulmoides* cultured root could be grown for a long period of time by subculturing every four weeks, and used as an experimental material. The grown new root was cut into pieces having a length of approximately 1.5 cm, and transformed with pBIsGFP-TPL1 by an *Agrobacterium* method. In the Agrobacterium method, the *Agrobacterium tumefaciens* LBA4404 strain was used. In order to promote infection with Agrobacteria, the cultured root was treated with ultrasonic waves for 20 minutes before infection. The cultured root infected with Agrobacteria was transferred onto a callus induction agar medium (MS medium, 1 µM 2-iP, 1 µM NAA), calluses were induced, and then a transformed *Eucommia ulmoides* callus was selected. The transformed callus was selected by use of a GFP signal. Next, the selected transformed callus was transferred onto a root induction medium (MS medium, 1 µM NAA), and roots were differentiated and grown from the callus. Here, among the transformed *Eucommia ulmoides* cultured roots obtained, 20 lines were maintained and used for analysis.

Analysis of Transformed *Eucommia ulmoides* Cultured Root: 1

Figure 5:
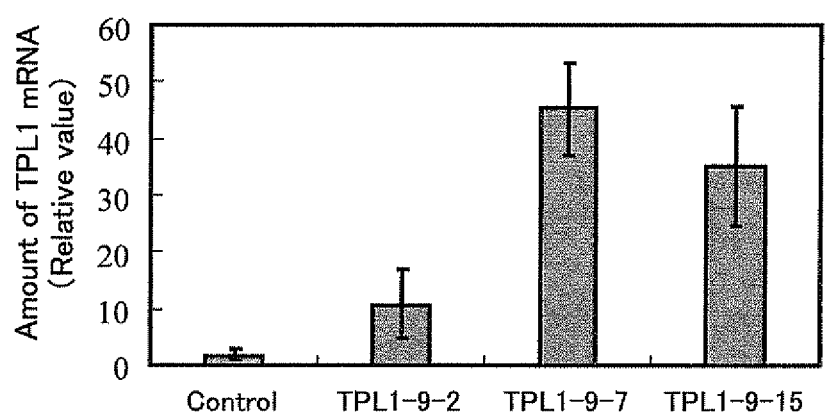
FIG. 5 is a graph showing the amount of TPL1 mRNA.

The amount of TPL1 mRNA for 20 lines of the transformed *Eucommia ulmoides* cultured roots was quantified by Real-time PCR (FIG. 5). RNA was extracted from the transformed *Eucommia ulmoides* cultured roots using an RNeasy Plant Mini Kit (manufactured by Qiagen). First, contaminating DNA was removed using RNase-Free DNase I (manufactured by Qiagen). Next, the concentration of the RNA sample was measured. At the same time, six concentrations of samples (RNA concentration: 400, 100, 25, 6.25, 1.56 and 0.39 ng/µL for a calibration curve were prepared. Then, cDNA was prepared from the RNA sample extracted from the transformed *Eucommia ulmoides* cultured roots and the calibration curve samples, using a High Capacity Reverse Transcription Kit (manufactured by Applied Biosystems). Real-time PCR was performed using this cDNA as a template, and the ABI Prism 7300 Sequence Detection System (manufactured by Applied Biosystems) by the SYBR Green method. The base sequences of the primers used were as follows. In the Realtime PCR, a cycle of two minutes at 50° C. and then ten minutes at 95° C. was performed once, and then a cycle of 15 seconds at 95° C. and then one minute at 60° C. was performed 40 times. Next, a 15-second reaction at 95° C., a one-minute reaction at 60° C., a 15-second reaction at 95° C., and then a 15-second reaction at 60° C. were performed, and the dissociation status was observed.

Primer Set for TPL1 Quantification

| Sense primer: | AAGGAGCTCAACTCACTGAGAGC | (SEQ ID NO: 28) |
| Antisense primer: | AATGCACCAACCCAACACAG | (SEQ ID NO: 29) |

Primer Set for Calibration Curve (Detection of Internal Reference Gene EF1α).

| Sense primer: | CCGAGCGTGAACGTGGTAT | (SEQ ID NO: 30) |
| Anti primer: | TAGTACTTGGTGGTTTCGAATTTCC | (SEQ ID NO: 31) |

Analysis of Transformed *Eucommia ulmoides* Cultured Roots: 2

Figure 6:
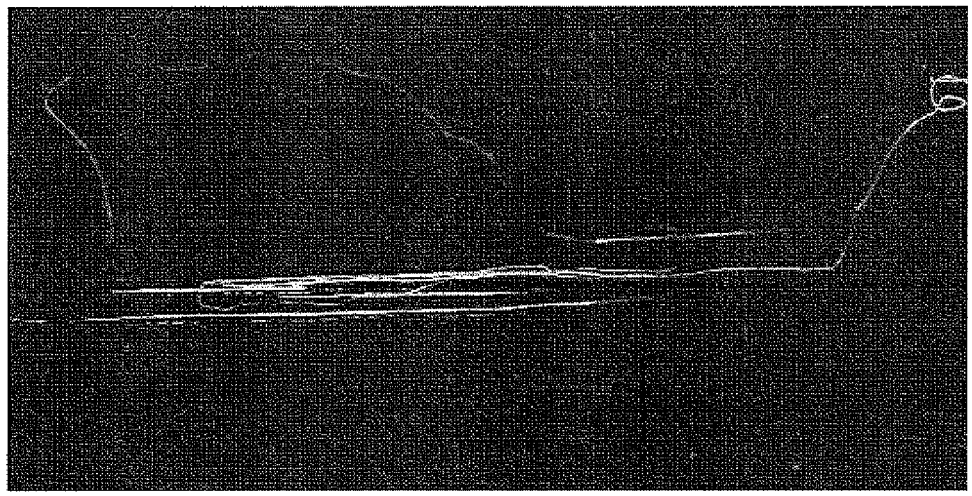
FIG. 6 is an image obtained using a real spectral imaging microscope showing the distribution of rubber produced inside a cultured root of transformed *Eucommia ulmoides*.
Figure 7:
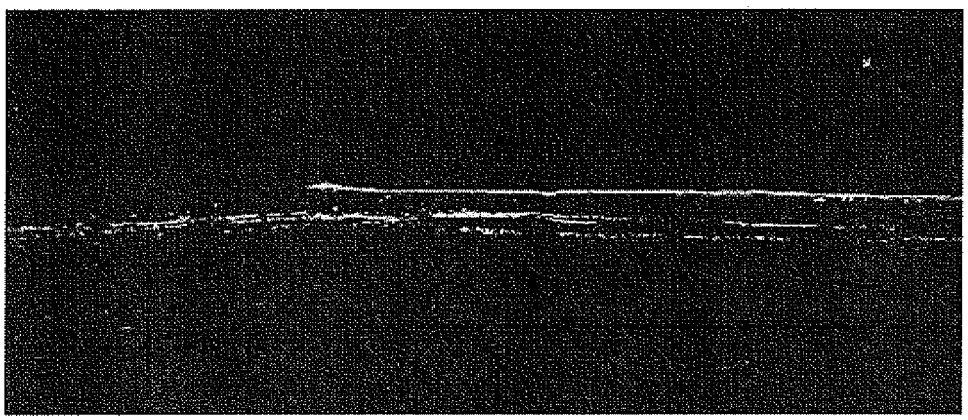
FIG. 7 is an image obtained using a real spectral imaging microscope showing the distribution of rubber produced inside a cultured root of wild-type *Eucommia ulmoides*.

The distributions of rubber produced inside the transformed *Eucommia ulmoides* cultured root TPL1-9-7 (FIG. 6), which had the largest amount of TPL1 mRNA, and a wild-type *Eucommia ulmoides* cultured root (FIG. 7) were evaluated using a real spectral imaging microscope (SCLSM). Separated fluorescence images of the cultured roots were acquired using DIGITAL ECLIPSE C1si manufactured by Nikon Corporation as the SCLSM. The fluorescence separation was performed using a reference spectrum with EZ-C1 3.40 software manufactured by Nikon Corporation. The reference spectrum was acquired as follows. Fluorescence spectral images of fibrous trans-polyisoprene taken from *Eucommia ulmoides* bark for herbal medicine and stained with Nile red, and a cross-sectional piece of the bark of a current year's branch of *Eucommia ulmoides* stained with Nile red (for staining particulate liposoluble substance) and Fluorescent Brightener 28 (for staining cell walls) were acquired using DIGITAL ECLIPSE C1si, the fluorescence spectra of ten regions of interest (ROI) assigned by EZ-C1 3.40 were measured, and their average value was taken as the reference spectrum. In the acquisition of the Nile red-derived fluorescence spectra, spectra in the range of 418 to 578 nm were acquired using a solid-state laser (488 nm, 20 mW). In the acquisition of the Fluorescent Brightener 28-derived fluorescence spectra, spectra in the wavelength range of 498 to 658 nm were acquired using a BD laser (408 nm, 17 mW). The fluorescence maximum wavelengths of the acquired reference spectra were 545 nm (Nile red-derived, trans-polyisoprene), 575 nm (Nile red-derived, particulate liposoluble substance), and 450 nm (Fluorescent Brightener 28-derived, cell wall). In the acquisition of the separated fluorescence images of the cultured roots, spectra in the range of 423 to 723 nm were acquired using a solid-state laser and a BD laser.

As a result, it was found that the rubber chain of the transformed *Eucommia ulmoides* cultured root TPL1-9-7 was 1.4 times as long as that of the wild-type *Eucommia ulmoides* cultured root. Furthermore, while the rubber was accumulated in the form of granules in the wild-type *Eucommia ulmoides* cultured root, the rubber was changed into the form of fibers in the transformed *Eucommia ulmoides* cultured root TPL1-9-7. Accordingly, it was found that TPL1 participate in the control of the rubber chain length of *Eucommia ulmoides*.

Example 6

Transformation of *Nicotiana tabacum*

Construction of Plant-Transforming TPL Expression Vector

Figure 8:
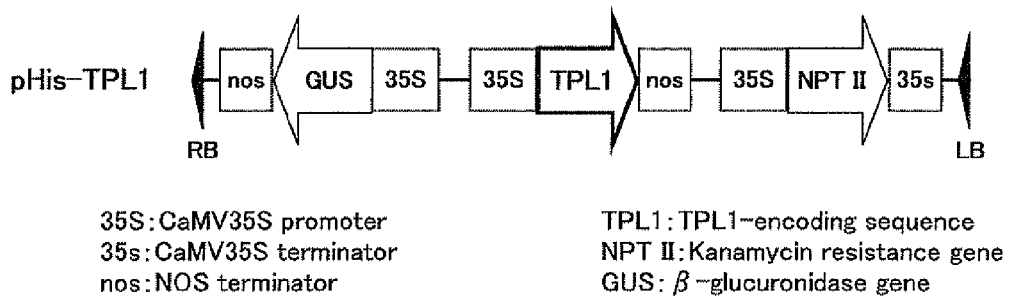
FIG. 8 is a schematic diagram showing the structure of plant-transforming TPL expression vector pHis-TPL1.

A TPL1 expression cassette having a fragment of the sequence encoding TPL1 protein derived from pBluescript-TPL1 described in Example 4, and the CaMV35S promoter fragment and the NOS terminator fragment derived from pBI221 (manufactured by Clontech) was constructed, and inserted into the multicloning site of plant-transforming vector pCAMBIA2301 (manufactured by Cambia), and, thus, plant-transforming TPL expression vector pHis-TPL1 was constructed (FIG. 8). pCAMBIA2301 contains a kanamycin resistance gene and the β-glucuronidase gene.

Transformation of *Nicotiana tabacum*

Leaves (leaf disks) of *Nicotiana tabacum* cv *Xanthi* were transformed with pHis-TPL1 by the Agrobacterium method. Furthermore, transformation with pBIsGFP was performed as a control. In the *Agrobacterium* method, the *Agrobacterium tumefaciens* LBA4404 strain was used.

Analysis of Transformed *Nicotiana tabacum*

Figure 9:
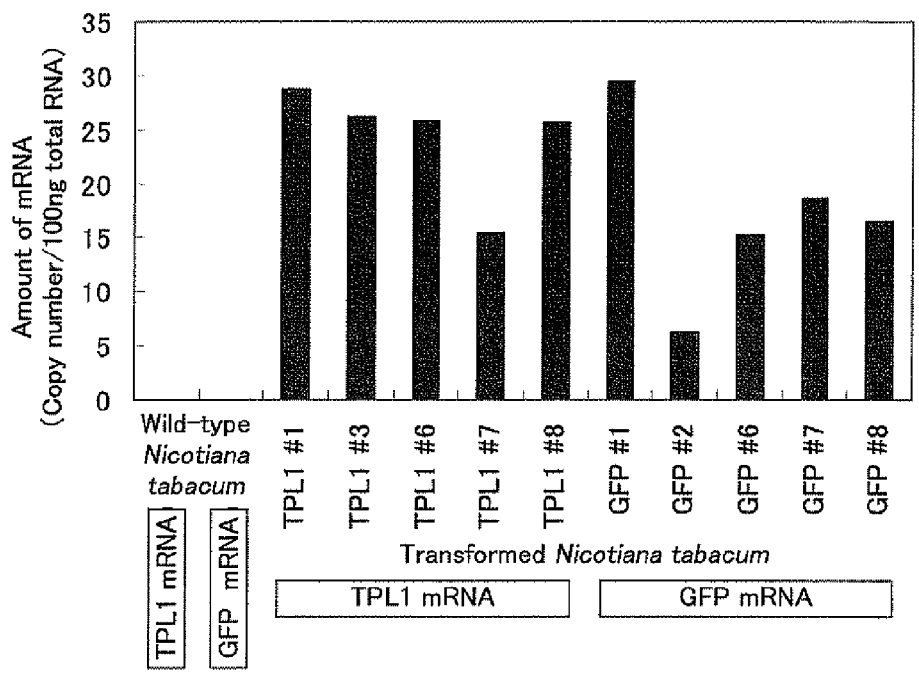
FIG. 9 is a graph showing the amount of TPL1 mRNA and GFP mRNA.

The amounts of TPL1 and GFP (control) mRNA of the transformed *Nicotiana tabacum* (TPL1 transformed *Nicotiana tabacum*) obtained by transformation with pHis-TPL1 and the transformed *Nicotiana tabacum* (GFP transformed *Nicotiana tabacum*) obtained by transformation with pBIs-GFP were measured by Realtime PCR (FIG. 9). The experimental method and conditions were as in Example 5. Next, mature leaves were collected from the TPL1 transformed *Nicotiana tabacum* TPL1 #8 and the GFP transformed *Nicotiana tabacum* GFP #1, which had a large amount of mRNA, and wild-type *Nicotiana tabacum* before formation of flower buds, and subjected to Soxhlet-extraction with ethanol, and then Soxhlet-extraction with toluene. Polyisoprene was obtained by extraction with toluene. The extract was analyzed by size-exclusion chromatography (SEC). A Hitachi 7000 series liquid chromatograph (manufactured by Hitachi, Ltd.) was used. A PLgel Mini Mixed B (10 μm, 250×internal diameter 4.6 mm, manufactured by Polymer Laboratories, Shropshire, England) was used as the column, and THF was used as the eluent. Analysis was performed at a column temperature of 40° C. and a flow rate of 0.2 mL/min, and the ultraviolet absorption (210 nm) was detected. Seven types of cis-1,4-polyisoprene (Mn=1199400, Mw/Mn=1.10; Mn=138000, Mw/Mn=1.05; Mn=30000, Mw/Mn=1.04; Mn=12000, Mw/Mn=1.04; Mn=6000, Mw/Mn=1.04; Mn=2560, Mw/Mn=1.08; Mn=1150, Mw/Mn=1.11) manufactured by Polymer Source were used as samples for a calibration curve in the SEC analysis. An SIC-480II manufactured by System Instruments and analysis software were used to collect data, generate a calibration curve, and calculate a molecular weight distribution.

Figure 10:
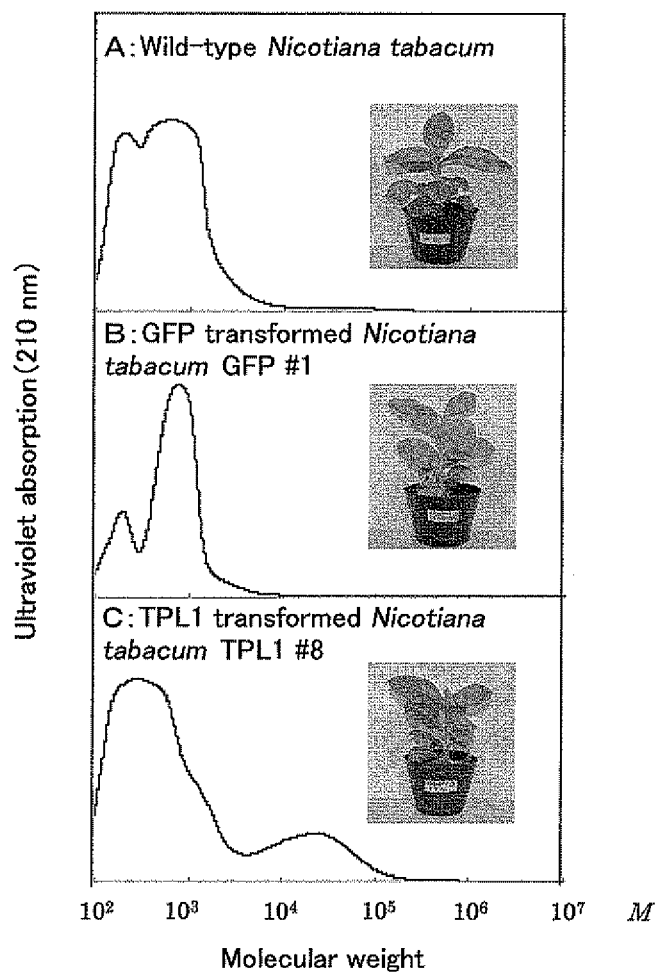
FIG. 10 are graphs showing the results of SEC analysis for wild-type *Nicotiana tabacum* (A), GFP transformed *Nicotiana tabacum* GFP #1 (B) and TPL1 transformed *Nicotiana tabacum* TPL1 #8 (C), with insertion of photographs showing the status of leaves of *Nicotiana tabacum* subjected to analysis.
Figure 11:
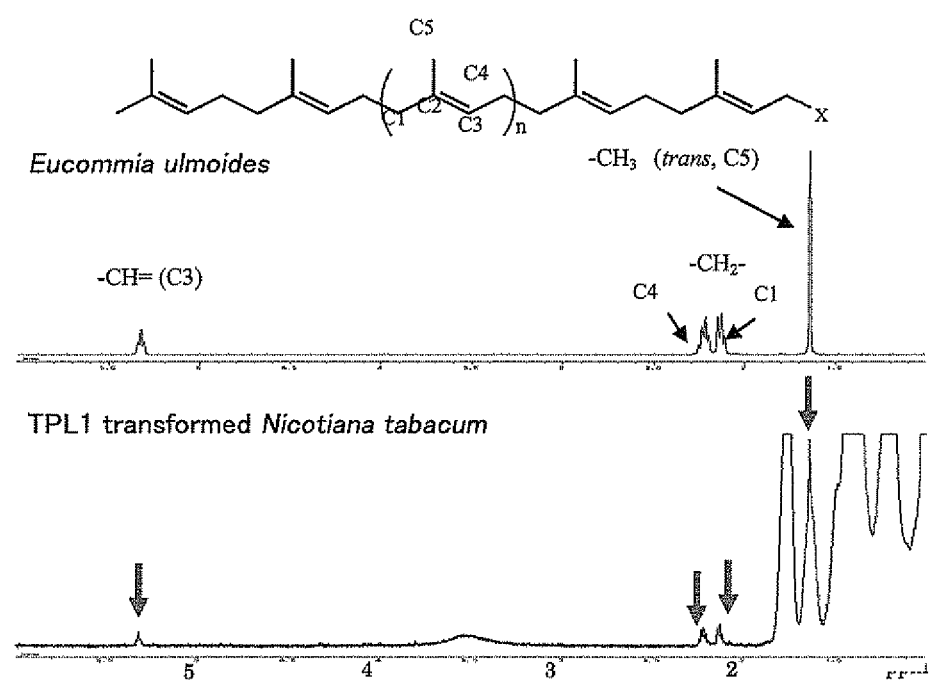
FIG. 11 are spectra showing the results of $^1$H-NMR analysis of mature leaf extracts for *Eucommia ulmoides* (upper) and TPL1 transformed *Nicotiana tabacum* (lower), with insertion of a structural formula of trans-1,4-polyisoprene.

As a result, it was confirmed that TPL1 transformed *Nicotiana tabacum* TPL1 #8 had high-molecular weight components with a molecular weight of $10^4$ to $10^5$ (FIG. 10C). It was also confirmed that the TPL1 transformed *Nicotiana tabacum* TPL1 #1, #3, #6 and #7, having a large amount of TPL1 mRNA, similarly had high-molecular weight components with a molecular weight of $10^4$ to $10^5$. On the other hand, it was confirmed that the GFP transformed *Nicotiana tabacum* GFP #1 and the wild-type *Nicotiana tabacum* did not have a high-molecular weight component (FIGS. 10A and 10B). It was also confirmed that the GFP transformed *Nicotiana tabacum* GFP #2 and #6 to #8, having a large amount of GFP mRNA, did not have a high-molecular weight component. Next, high-molecular weight fractions with a molecular weight of $10^4$ to $10^5$ according to SEC analysis were separated from the mature leaf extract of the TPL1 transformed *Nicotiana tabacum* TPL1 #8, and subjected to structure analysis by $^1$H-NMR analysis using a Varian Unity-INOVA 600 Spectrometer (manufactured by Varian). As a result, it was confirmed that the high-molecular weight fractions with a molecular weight of $10^4$ to $10^5$ contained trans-1,4-polyisoprene as in the rubber of *Eucommia ulmoides* (FIG. 11). Accordingly, it was found that TPL1 is a trans-1,4-polyisoprene synthase, and is a long-chain trans-prenyl diphosphate synthase.

According to the present invention, when a plant is transformed with an expression vector containing a long-chain trans-prenyl diphosphate synthase gene, a plant that has an increased content of trans-1,4-polyisoprene can be obtained. According to the present invention, the content of trans-1,4-polyisoprene in a plant can be increased, and trans-1,4-polyisoprene can be effectively produced using such a plant. In particular, trans-1,4-polyisoprene can be easily extracted from the peel of transformed *Eucommia ulmoides* that has a higher content of trans-1,4-polyisoprene, and, thus, trans-1,4-polyisoprene can be easily provided as an industrial raw material.

What is claimed is:

1. An expression vector containing a long-chain trans-prenyl diphosphate synthase gene comprising a DNA having at least one base sequence selected from the group consisting of a base sequence from positions 42 to 1088 of the base sequence of SEQ ID NO: 3 or a complementary sequence thereof, and a base sequence from positions 91 to 1140 of the base sequence of SEQ ID NO: 5 or a complementary sequence thereof.

2. A plant transformed with the expression vector of claim 1.

3. The plant of claim 2, wherein the plant is *Eucommia ulmoides*.

4. The plant of claim 2, wherein the plant is *Nicotiana tabacum*.

5. A method for increasing the amount of trans-1,4-polyisoprene contained in a plant, comprising the step of transforming the plant using the expression vector of claim 1.

6. A method for producing trans-1,4-polyisoprene, comprising the steps of:
    cultivating the plant of claim 2; and
    recovering the trans-1,4-polyisoprene from the cultivated plant.

7. A method for producing trans-1,4-polyisoprene, comprising the steps of:
    cultivating the plant of claim 3; and
    recovering the trans-1,4-polyisoprene from the cultivated plant.

8. A method for producing trans-1,4-polyisoprene, comprising the steps of:
    cultivating the plant of claim 4; and
    recovering the trans-1,4-polyisoprene from the cultivated plant.

* * * * *

UNITED STATES PATENT AND TRADEMARK OFFICE
CERTIFICATE OF CORRECTION

PATENT NO.       : 9,127,286 B2                          Page 1 of 1
APPLICATION NO.  : 12/550863
DATED            : September 8, 2015
INVENTOR(S)      : Yoshihisa Nakazawa et al.

It is certified that error appears in the above-identified patent and that said Letters Patent is hereby corrected as shown below:

Title Page, Item (56) Column 1, OTHER PUBLICATIONS, Line 3, delete "Accesion" and insert -- Accession --

Signed and Sealed this
Nineteenth Day of July, 2016

Michelle K. Lee
*Director of the United States Patent and Trademark Office*